United States Patent
Yamashita

(10) Patent No.: US 7,124,264 B2
(45) Date of Patent: Oct. 17, 2006

(54) STORAGE SYSTEM, CONTROL METHOD FOR STORAGE SYSTEM, AND STORAGE CONTROL UNIT

(75) Inventor: Shinichiro Yamashita, Fujisawa (JP)

(73) Assignee: Hitachi, Ltd., Tokyo (JP)

( * ) Notice: Subject to any disclaimer, the term of this patent is extended or adjusted under 35 U.S.C. 154(b) by 292 days.

(21) Appl. No.: 10/806,986

(22) Filed: Mar. 22, 2004

(65) Prior Publication Data

US 2005/0148891 A1 Jul. 7, 2005

(30) Foreign Application Priority Data

Jan. 7, 2004 (JP) ............................ 2004-002037

(51) Int. Cl.
*G06F 11/16* (2006.01)

(52) U.S. Cl. .................. 711/162; 711/147; 711/112; 711/114; 711/148; 711/153; 711/161; 711/165; 707/202; 707/204; 714/6; 714/15; 714/20; 714/47

(58) Field of Classification Search .................. None
See application file for complete search history.

(56) References Cited

U.S. PATENT DOCUMENTS

| | | | |
|---|---|---|---|
| 6,173,377 B1 * | 1/2001 | Yanai et al. ............... 711/162 |
| 6,601,187 B1 | 7/2003 | Sicola et al. | |
| 6,629,264 B1 | 9/2003 | Sicola et al. | |
| 6,732,243 B1 | 5/2004 | Busser et al. | |
| 2002/0095489 A1 * | 7/2002 | Yamagami .................. 709/224 |
| 2003/0033523 A1 | 2/2003 | McNulty et al. | |
| 2003/0187947 A1 | 10/2003 | Lubbers et al. | |
| 2004/0078644 A1 | 4/2004 | Fujibayashi et al. | |

FOREIGN PATENT DOCUMENTS

WO    WO04/051479 A2    6/2004

* cited by examiner

*Primary Examiner*—Mano Padmanabhan
*Assistant Examiner*—Patrick M Moore
(74) *Attorney, Agent, or Firm*—Townsend and Townsend and Crew LLP

(57) ABSTRACT

The present invention relates to a storage system, including a first storage unit having a first storage volume for storing data, and a second storage unit having a second storage volume communicably connected with the first storage unit, wherein the first storage unit further comprises a replication data transmission unit for transmitting the replication of data to a second storage unit when the data is written to the first storage volume, the second storage unit further comprises a replication data reception unit for writing the replication of the data transmitted by the replication data transmission unit to the second storage volume, the first storage unit further comprises a disk heart beat write unit for repeatedly writing a first heart beat message to the first storage volume at intervals within a predetermined time, and the second storage unit further comprise a disk heart beat detection unit for detecting the replication of the first heart beat message to be written to the second storage volume by the replication data reception unit.

14 Claims, 19 Drawing Sheets

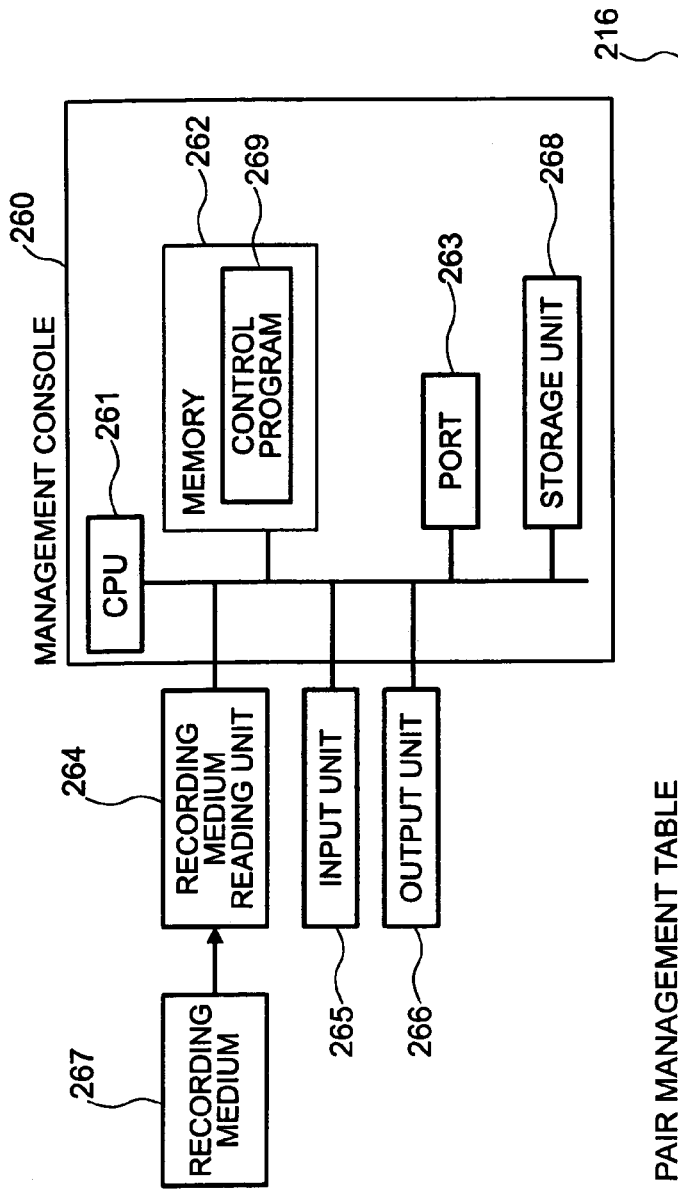

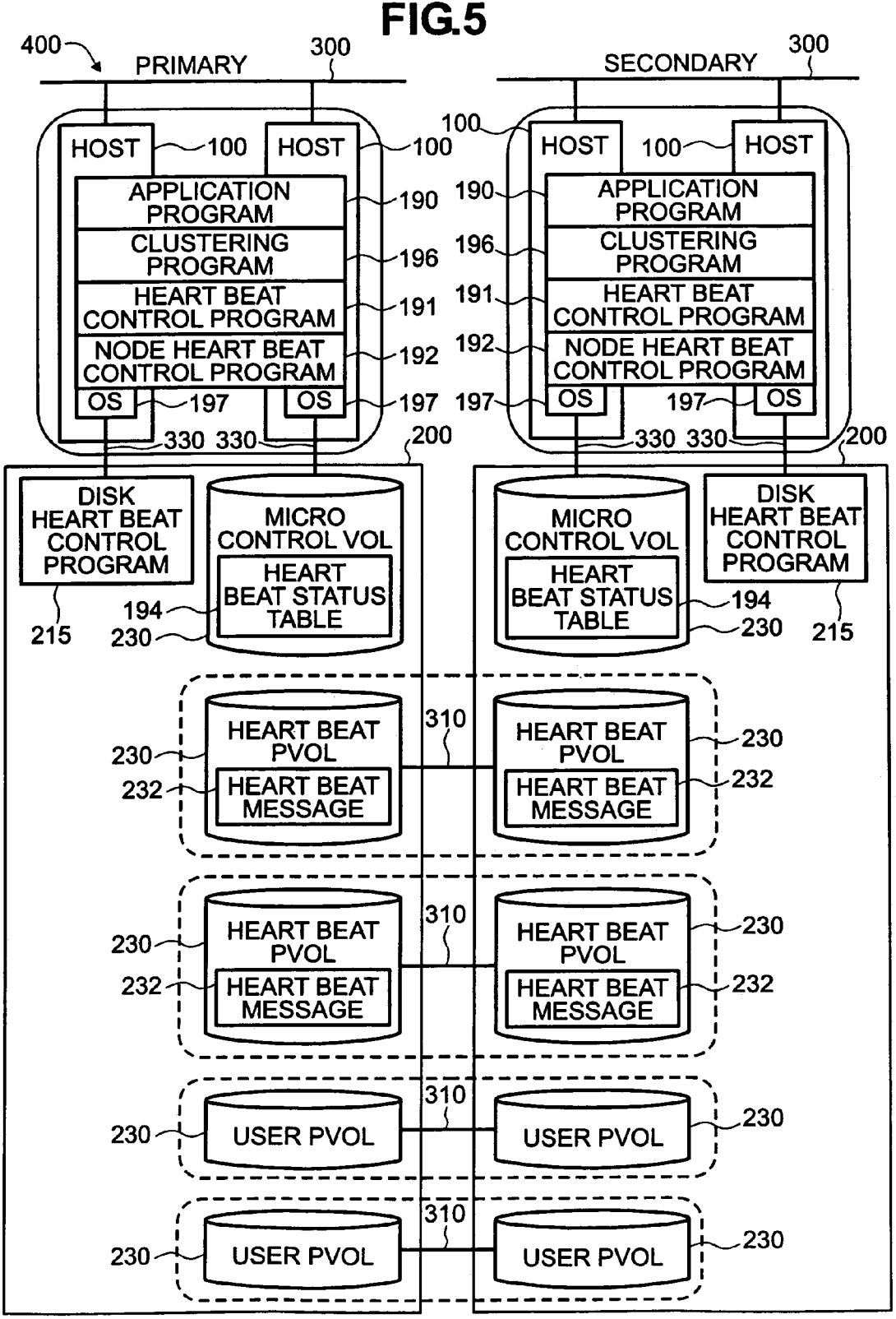

FIG.6

ACTIVATION/INACTIVATION MESSAGE (195)

| ACTIVATION/INACTIVATION TYPE |
|---|
| DISK HEART BEAT/NODE HEART BEAT |
| LOCAL DEVICE ADDRESS |
| REMOTE DEVICE ADDRESS |

FIG.7

HEART BEAT STATUS TABLE (194)

NODE HEART BEAT STATUS
P/S TYPE (1)
LOCAL DEVICE ADDRESS (1)
REMOTE DEVICE ADDRESS (1)
DEVICE STATUS (1)
P/S TYPE (2)
LOCAL DEVICE ADDRESS (2)
REMOTE DEVICE ADDRESS (2)
DEVICE STATUS (2)
:
DISK HEART BEAT STATUS
P/S TYPE (3)
LOCAL DEVICE ADDRESS (3)
REMOTE DEVICE ADDRESS (3)
DEVICE STATUS (3)
P/S TYPE (4)
LOCAL DEVICE ADDRESS (4)
REMOTE DEVICE ADDRESS (4)
DEVICE STATUS (4)
:

|  |  | NODE HEART BEAT SIGNAL | |
|---|---|---|---|
|  |  | OK | NG |
| DISK HEART BEAT SIGNAL | OK | ① | ② |
|  | NG | ③ | ④ |

| INFORMATION PROCESSING UNIT A | STORAGE UNIT A | | INPUT/ OUTPUT PATH A | SECOND NETWORK | INFORMATION PROCESSING UNIT B | STORAGE UNIT B | | INPUT/ OUTPUT PATH B |
|---|---|---|---|---|---|---|---|---|
| | DISK CONTROL UNIT A | P-VOL | | | | DISK CONTROL UNIT B | S-VOL | |
| ○ | ○ | ○ | ○ | ○ | ○ | ○ | ○ | ○ |
| ◄ | ○ | ○ | ◄ | ○ | ○ | ○ | ○ | ○ |
| ○ | ◄ | ○ | ○ | ○ | ○ | ○ | ○ | ○ |
| ◄ | ◄ | ◄ | ◄ | ◄ | ◄ | ◄ | ◄ | ◄ |

| | INFORMATION PROCESSING UNIT A | DISK CONTROL UNIT A | STORAGE UNIT A | | INPUT/ OUTPUT PATH A | SECOND NETWORK | INFORMATION PROCESSING UNIT B | STORAGE UNIT B | | | INPUT/ OUTPUT PATH B |
|---|---|---|---|---|---|---|---|---|---|---|---|
| | | | P-VOL FOR NODE HB | P-VOL FOR DISK HB | | | | DISK CONTROL UNIT B | S-VOL FOR NODE HB | S-VOL FOR DISK HB | |
| ① | ○ | ○ | ○ | ○ | ○ | ○ | ○ | ○ | ○ | ○ | ○ |
| ② | ◀ | ○ | ◀ | ○ | ◀ | ○ | ○ | ○ | ◀ | ○ | ○ |
| ③ | ○ | ◀ | ○ | ◀ | ○ | ○ | ○ | ○ | ◀ | ◀ | ○ |
| ④ | ◀ | ◀ | ◀ | ◀ | ◀ | ◀ | ◀ | ◀ | ◀ | ◀ | ◀ |

FIG.21

|  |  | NODE HEART BEAT SIGNAL 1 | | | |
|---|---|---|---|---|---|
|  |  | OK | | NG | |
|  |  | NODE HEART BEAT SIGNAL 2 | | NODE HEART BEAT SIGNAL 2 | |
|  |  | OK | NG | OK | NG |
| DISK HEART BEAT SIGNAL | OK | ① | ② | ③ | ④ |
|  | NG | ⑤ | ⑥ | ⑦ | ⑧ |

FIG.22

| | INFORMATION PROCESSING UNIT A | STORAGE UNIT A | | | | INPUT/OUTPUT PATH A | SECOND NETWORK | INFORMATION PROCESSING UNIT B | STORAGE UNIT B | | | | INPUT/OUTPUT PATH B |
|---|---|---|---|---|---|---|---|---|---|---|---|---|---|
| | | DISK CONTROL UNIT A | P-VOL 1 FOR NODE HB | P-VOL 2 FOR NODE HB | P-VOL FOR DISK HB | | | | DISK CONTROL UNIT B | S-VOL 1 FOR NODE HB | S-VOL 2 FOR NODE HB | S-VOL FOR DISK HB | |
| ① | ○ | ○ | ○ | ○ | ○ | ○ | ○ | ○ | ○ | ○ | ○ | ○ | ○ |
| ② | ○ | ○ | ○ | ◀ | ○ | ○ | ○ | ○ | ○ | ○ | ◀ | ○ | ○ |
| ③ | ○ | ○ | ◀ | ○ | ○ | ○ | ○ | ○ | ○ | ◀ | ○ | ○ | ○ |
| ④ | ◀ | ○ | ◀ | ◀ | ○ | ◀ | ○ | ○ | ○ | ◀ | ◀ | ○ | ○ |
| ⑤ | ○ | ○ | ○ | ○ | ◀ | ○ | ○ | ○ | ○ | ○ | ○ | ◀ | ○ |
| ⑥ | ○ | ○ | ○ | ◀ | ◀ | ○ | ○ | ○ | ○ | ○ | ◀ | ◀ | ○ |
| ⑦ | ○ | ○ | ◀ | ○ | ◀ | ○ | ○ | ○ | ○ | ◀ | ○ | ◀ | ○ |
| ⑧ | ◀ | ◀ | ◀ | ◀ | ◀ | ◀ | ◀ | ◀ | ◀ | ◀ | ◀ | ◀ | ◀ |

STORAGE SYSTEM, CONTROL METHOD FOR STORAGE SYSTEM, AND STORAGE CONTROL UNIT

CROSS-REFERENCE TO RELATED APPLICATION

This application relates to and claims priority from Japanese Patent Application No. 2004-002037, filed on Jan. 7, 2004, the entire disclosure of which is incorporated herein by reference.

BACKGROUND OF THE INVENTION

1. Field of the Invention

The present invention relates to a storage system, a control method for a storage system, and a storage control unit.

2. Description of the Related Art

In order to avoid the loss of data stored in a storage unit constituting a computer system when such a disaster as an earthquake occurs, a technology called "replication" is used in the recent advances of information technology. Replication is a technology for storing the replication of data, which is stored in a storage volume of a storage unit of a computer system at a main site, to a storage volume in a storage unit of a storage system at a remote site.

In the case when a computer system at a remote site detects that the computer system at the main site has shut down, a technology for the computer system at the remote site to "take over" the information processing that the computer at the main site has been executing was developed.

The information processing unit of the computer system at the main site repeatedly transmits a predetermined data called a "heart beat message" to the computer system at the remote site at intervals within a predetermined time. A technology to transmit this heart beat message using replication technology was also developed.

In this case, the computer system at the remote site detects the interruption of transmission of the heart beat message from the main site, by which the occurrence of an abnormality to the computer at the main site is detected. However, when the transmission of the heart beat message from the main site is interrupted by an abnormality of the storage unit at the main site, the computer system at the remote site cannot specify that it is the storage unit at the main site where the abnormality occurred.

SUMMARY OF THE INVENTION

With the foregoing in view, it is an object of the present invention to provide a storage system, a control method for a storage system, and a storage control unit.

To solve the above problem, the present invention relates to a storage system, comprising a first storage unit that has a first storage volume for storing data, and a second storage unit that is connected communicably with the first storage unit and has a second storage volume for storing data, wherein the first storage unit further comprises a replication data transmission unit for transmitting the replication of data to the second storage unit when the data is written to the first storage volume, the second storage unit further comprises a replication data reception unit for receiving the replication of the data transmitted by the replication data transmission unit and writing the replication of the data to the second storage volume, the first storage unit further comprises a disk heart beat write unit for repeatedly writing a first heart beat message to the first storage volume at intervals within a predetermined time, and the second storage unit further comprises a disk heart beat detection unit for detecting the replication of the first heart beat message to be written to the second storage volume by the replication data reception unit.

In this case, it is also possible that a first information processing unit is communicably connected to the first storage unit and a second information process unit is communicably connected to the second storage unit, the first information processing unit further comprises a node heart beat write request unit for repeatedly transmitting a request to write a second heart beat message to the first storage volume, to the first storage unit at intervals within a predetermined time, the first storage unit further comprises a node heart beat write unit for writing the second heart beat message to the first storage volume according to the write request of the second heart beat message, the second storage unit further comprises a node heart beat transmission unit for transmitting the replication of the second heart beat message, to be written to the second storage volume by the replication data reception unit, to the second information processing unit, and the second information processing unit further comprises a node heart beat detection unit for detecting the replication of the second heart beat message to be transmitted by the node heart beat transmission unit.

The first heart beat message is also referred to as a "disk heart beat signal", and the second heart beat message as "node heart beat signal" herein below.

Problems that the present application discloses and the solutions thereof will be clarified through the preferred embodiments and drawings.

The present invention can provide a storage system, a control method for a storage system, and a storage control unit.

BRIEF DESCRIPTION OF THE DRAWINGS

FIG. 3 is a block diagram depicting the configuration. of a management console according to the present embodiment;

FIG. 4 is a diagram showing a pair management table according to the present embodiment;

FIG. 5 is a block diagram depicting the general configuration of a storage system according to the present embodiment;

FIG. 6 is a diagram showing an activation/deactivation message according to the present embodiment;

FIG. 7 is a diagram showing a heart beat status table according to the present embodiment;

FIG. 17 is a diagram showing heart beat decision table according to the present embodiment;

FIG. 19 is a diagram depicting a heart beat decision table according to the present embodiment;

FIG. 21 is a diagram showing a heart beat decision table according to the present embodiment;

FIG. 22 is a diagram showing a heart beat decision table according to the present embodiment.

DESCRIPTION OF THE PREFERRED EMBODIMENTS

General Configuration Example

Figure 1:
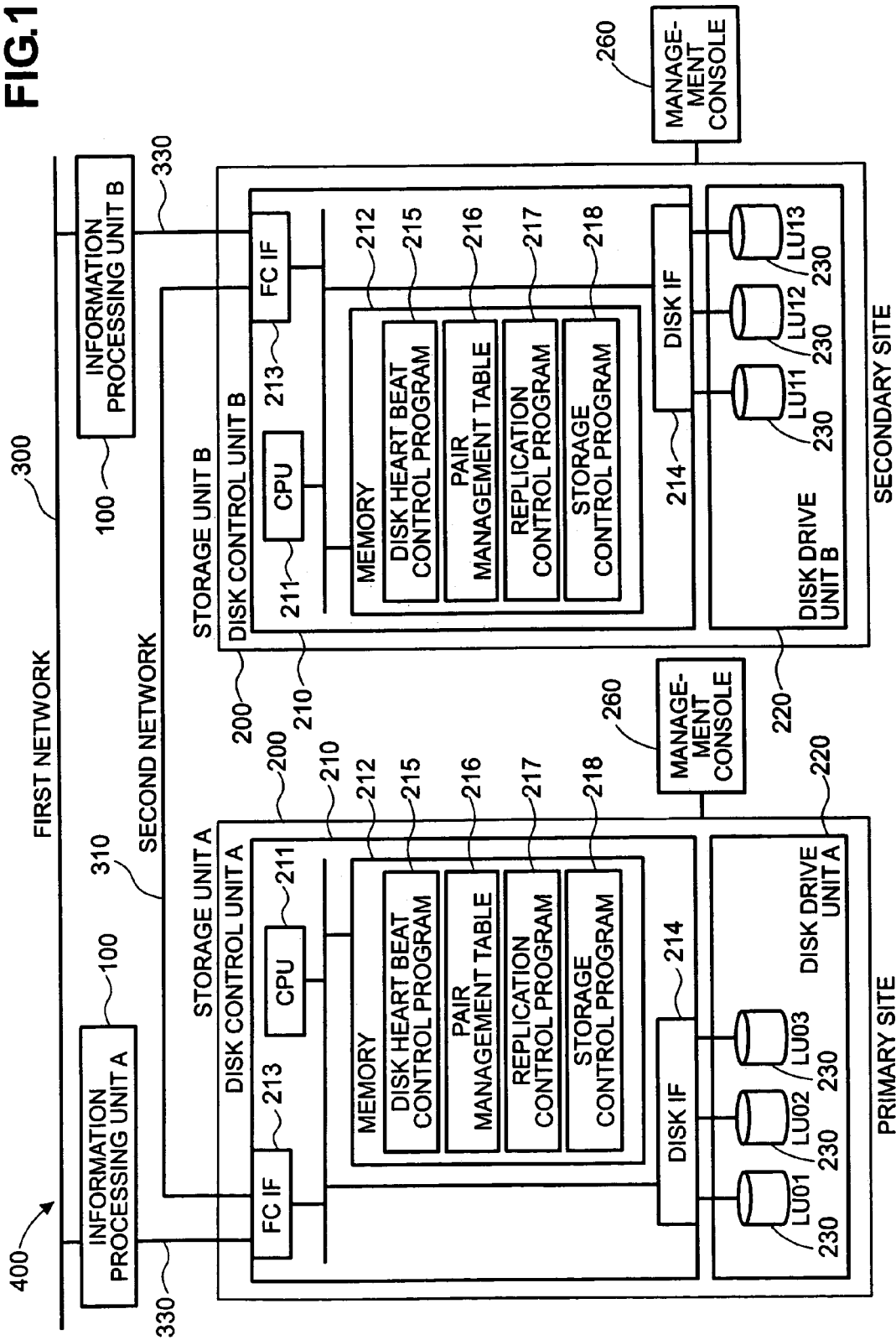
FIG. 1 is a block diagram depicting the general configuration of a storage system according to the present embodiment.

FIG. 1 shows a block diagram depicting the general configuration of a storage system 400 according to the present invention.

The storage system 400 according to the present invention is comprised of an information processing unit A (first information processing unit) 100, storage unit A (first storage unit) 200, information processing unit B (second information processing unit) 100 and storage unit B (second storage unit) 200.

The information processing unit A (100) and the storage unit A. (200) constitute a computer system (first computer system) installed at a main site (primary site). The information processing unit B (100) and the storage unit B (200) constitute a computer system (second computer system) installed at a remote site (secondary site).

The information processing unit. A (100) is an information equipment for providing various information processing services using the storage resources provided by the storage volume 230 of the storage unit A (200). The information processing services provided by the information processing unit A (100) are, for example, automatic deposit/withdrawal services of a bank and seat reservation services of an airline. The location where the information processing unit A (100) and the storage unit A (200) are installed is called a "main site".

The storage volume 230 is a storage area for storing data, and includes a physical volume, that is a physical storage area provided by a hard disk drive, for example, and a logical volume, that is a storage area which is logically set on the physical volume.

The information processing unit B (100), on the other hand, is an information equipment for taking over the information processing service, which the information processing unit A (100) installed at the main site has been executing, when the information processing unit A (100) cannot provide the information processing service due to a disaster, for example. At this time, the information processing unit B (100) provides the information processing service by using the storage resources provided by the storage volume 230 of the storage unit B (200). For this, the replicated data stored in the storage volume 230 of the storage unit A (200) is also stored in the storage volume 230 of the storage unit B (200). To store the replication of the data stored in the storage unit A (200) in the storage unit B (200), replication control is executed. When replication control is executed, data is written to the storage volume 230 of the storage unit A (200), then the storage unit A (200) transmits the replicated data to the storage unit B (200). The storage unit B (200) receives the replicated data which is transmitted from the storage unit A (200), and writes the replicated data to the storage volume 203 of the storage unit B (200). The replication control will be described later. The location where the information processing unit B (100) and the storage unit B (200) are installed is called a "remote site".

The information processing unit B (100) not only takes over the information processing service provided by the information processing unit A (100), but also may provide its own information processing service. In this case, when the information service cannot be provided by the information processing unit B (100) due to a disaster, for example, the information processing unit A (100) may take over the information processing service provision. In this case, for both of these two computer systems, the local computer system becomes a computer system installed at a main site, and the other computer system becomes a computer system installed at a remote site. Here, however, to simplify description, the location where the information processing unit A (100) and the storage unit A (200) are installed is regarded as the main site, and the location where the information processing unit. B (100) and the storage unit B (200) are installed is regarded as the remote site.

The information processing unit A (100) installed at the main site and the information processing unit B (100) installed at the remote site are communicably connected via the first network 300. The storage unit A (200) installed at the main site and the storage unit B (200) installed at the remote site are communicably connected via the second network 310. The above mentioned replication control is executed by transmitting the replication of the data via the second network 310. The information processing unit A (100) and the storage unit A (200) are communicably connected via the input/output path A-330. The information processing unit B (100) and the storage unit B (200) are also communicably connected via the input/output path B-330.

The first network 300 can be a LAN (Local Area Network or a WAN (Wide Area Network based on TCP/IP (Transmission Control Protocol/Internet Protocol) communication protocol, for example.

The second network 310 can be a SAN (Storage Area Network) where communication is performed by fiber channel communication protocol, for example. The input/output path 330 can be a SAN where communication is performed by fiber channel communication protocol, for example. Certainly such communication protocols as FICON (Fiber Connection) (Registered Trademark), ESCON (Enterprise System Connection) (Registered Trademark), ACONARC (Advanced Connection Architecture) (Registered Trademark), FIBARC (Fiber Connection Architecture) (Registered Trademark) and iSCSI (internet Small Computer Systems Interface) can be used. By connecting the storage unit A (200) and the storage unit B (200) by the second network 310 using such a highly reliable communication protocol, data transmission/reception between the storage unit A (200) at the main site and the storage unit B (200) at the remote site can be performed with high reliability.

Information Processing Unit

Figure 2:
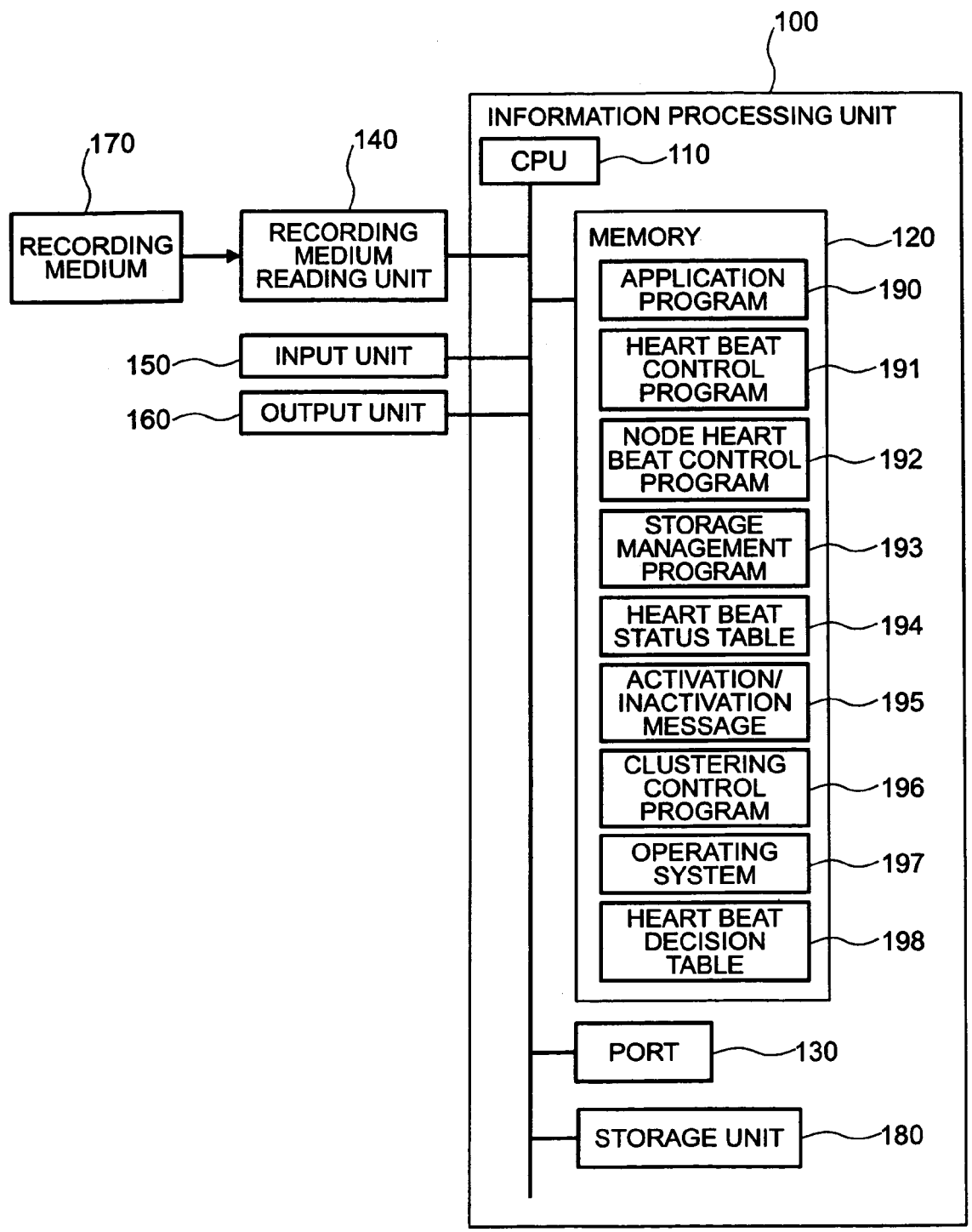
FIG. 2 is a block diagram depicting the configuration of an information processing unit according to the present embodiment.

FIG. 2 is a block diagram depicting the configuration of the information processing unit 100 according to the present embodiment. The information processing unit 100 according to the present embodiment includes the information processing unit A (100) and the information processing unit B (100), but both are referred to as information processing unit 100 unless a distinction is required, since the basic configuration thereof is the same.

The information processing unit 100 is comprised of a CPU 110, memory 120, port 130, recording medium reading unit 140, input unit 150, output unit 160 and storage unit 170.

The CPU 110 is in-charge of the overall control of the information processing unit 100, and provides the above mentioned various information processing services by executing the application programs 190 stored in the memory 120. The CPU 110 also executes the heart beat control program 191, node heart beat program 192, storage management program 193, clustering control program 196 and operating system 197 which are comprised of codes for performing various operations according to the present embodiment.

For example, the operation status decision unit and the operation status display unit are implemented by the CPU 110 executing the heart beat control program 191. Also the node heart beat write request unit, node heart beat detection unit and node heart beat creation unit are implemented by the CPU 110 executing the node heart beat control program 192, for example. Also the fail over control unit is implemented by the CPU 110 executing the clustering control program 196, for example. In the memory 120, the heart beat status table 194, activation/deactivation message 195 and heart beat decision table 198 are stored. Details on these will be described later. The heart beat control program 191, node heart beat control program 192, storage management program 193, clustering control program 196 and operating system 197 may be independent programs, or at least a part of these programs may be constructed by a same program. Each program may be comprised of a plurality of programs.

The recording medium reading unit 140 is a unit for reading programs and data recorded in the recording medium 170. The programs and data which are read are stored in the memory 120 or the storage unit 170. Therefore the heart beat control program 191, node heart beat control program 192, storage management program 193, clustering control program 196 and operating system 197, which are recorded in the recording medium 170, for example, can be read from the recording medium 170 using the recording medium reading unit 140, and can be stored in the memory 120 or the storage unit 180. For the recording medium 170, a flexible disk, magnetic tape, CD-ROM and semiconductor, for example, can be used. The recording medium reading unit 140 may be built into the information processing unit 100 or may be external. The storage unit 180 is a hard disk unit or a semiconductor storage unit, for example. The heart beat control program 191, node heart beat control program 192, storage management program 193, clustering control program 196, operating system 197, heart beat status table 194, activation/deactivation message 195 and heart beat decision table 198, for example, may be stored in the storage unit 180.

The input unit 150 is a user interface used for data input to the information processing unit 100 by an operator. The input unit 150 can be, for example, a keyboard or a mouse. The output unit 160 is a user interface used for output information. For the out unit 160, a display or a printer, for example, can be used. The port 130 is a unit for executing communication. For example, communication with another information processing unit 100 which is performed via the first network 300 and the transmission of data input/output request to the storage unit 200 may be executed via the port 130. Also the application program 190, heart beat control program 191, node heart beat control program 192, storage management program 193, clustering control program 196 and operation system 197, for example, may be received from another information processing unit 100 via the port 130, and stored in the memory 120 or the storage unit 180.

Storage Unit

The storage unit 200 according to the present embodiment will now be described with reference to FIG. 1. The storage unit 200 according to the present embodiment includes storage unit A (200) and the storage unit B (200), but both are referred to as storage unit 200 unless a distinction is required, since the basic configuration thereof is the same.

The storage unit 200 is comprised of a disk control unit (storage control unit) 210, a disk drive unit 220 and a management console 260.

The disk control unit 210 performs communication with the information processing unit 100 and another storage unit 200, and controls the read/write of the data to the storage volume 230 of the disk drive unit 220. For example, the disk control unit 210 receives a data write request from the information processing unit 100, and executes data write processing for the storage volume 230 of the disk drive unit 220.

The disk control unit 210 is comprised of a CPU 211, memory 212, FC I/F (Fibre Channel Interface) 213, and disk I/F (disk interface) 214.

The CPU 211 is in-charge of general control of the disk control unit 210, and executes the disk heart beat control program 215, replication control program 217 and storage control program 218, which are comprised of codes for executing various operations according to the present embodiment, and are stored in memory 212. For example, the disk heart beat write unit, disk heart beat detection unit and disk heart beat creation unit are implemented by the CPU 211 executing the disk heart beat control program 215. Also the replication data transmission unit and the replication data reception unit are implemented by the CPU 211 executing the replication control program 217, for example. Also the node heart beat write unit, node heart beat transmission unit and disk heart beat detection result transmission unit are implemented by the CPU 211 executing the storage control program 218, for example. In the memory 212, the pair management table 216 is stored. Details therefore will be described later. The disk heart beat control program 215, replication control program 217 and storage control program 218 may be independent programs, or at least a part of these programs may be constructed by a same program. Each program may be constructed by a plurality of programs. The FC I/F 213 has an interface function for communicating with the information processing unit 100 or another storage unit 200. The disk I/F 214 has an interface function for transmitting/receiving data with the disk drive unit 220.

The disk control unit A 210 and the disk control unit B 210, which are communicably connected via the second network 310, are also referred to as the storage control system.

The disk drive unit 220 has a storage volume 230 for storing data. The storage volume 230 is a storage area which includes the physical volume, that is a physical storage area provided by the hard disk drive, and a logical volume that is logically set on the physical volume. In FIG. 1, three storage volumes, LU01, LU02 and LU03 (first storage volume, third storage volume) (230) are shown for the storage unit A (200), and three storage volumes, LU11, LU12 and LU13 (second storage volume) (230) are shown for the storage unit B (200).

The management console 260 is an information equipment for maintenance and management of the storage unit 200. The management console 260 may be built into the storage unit 200 or may be external. The management console 260 may be a computer dedicated to the maintenance and management of the storage unit 200, or may be a general purpose computer which has maintenance and management functions.

FIG. 3 is a block diagram depicting the configuration of the management console 260. The management console 260 is comprised of a CPU 261, memory 262, port 263, recording medium reading unit 264, input unit 265, output unit 266 and storage unit 268.

The CPU 261 is in-charge of general control of the management console 260, and implements the maintenance and management functions of the storage unit 200 by executing the control program 269, stored in the memory 262, comprised of codes for performing various operations according to the present embodiments. The recording medium reading unit 264 is a unit for reading the program and data recorded in the recording medium 267. The program and data which were read are stored in the memory 262 or the storage unit 268. Therefore the control program 269, disk heart beat control program 215, replication control program 217 and storage control program 218, which are recorded in the recording medium 267, for example, can be read from the recording medium 267 using the recording medium reading unit 264, and stored in the memory 262 or the storage unit 268. For the recording medium 267, a flexible disk, CD-ROM, magnetic disk and semiconductor memory, for example, can be used. The recording medium reading unit 264 may be built into the management console 260 or may be external. The storage unit 268 may be a hard disk unit or a semiconductor storage unit, for example. The control program 269 may be stored in the storage unit 268.

The input unit 265 is a user interface used for data input to the management console 260 by an operator. For the input unit 265, a keyboard or a mouse, for example, can be used. The output unit 266 is a user interface for outputting information to the outside. For the output unit 266, a display or a printer, for example, can be used. The port 263 is a unit for communicating with the information processing unit 100 and the storage unit 200. By this, the control program 269, disk heart beat control program 215, replication control program 217 and storage control program 218 can be received from the information processing unit 100 via the port 263, and be stored in the memory 262 and the storage unit 268, for example. Also the disk heart beat control program 215, replication control program 217 and storage control program 218, which are stored in the memory 262 and the storage unit 268, can be transmitted to the disk control unit 210 via the port 263, and be stored in the memory 212 of the disk control unit 210.

The function of the management console 260 of the present embodiment may be installed in the information processing unit 100. In some cases the management console 260 may not be installed. In such cases, the maintenance and management of the storage unit 200 are performed using the information processing unit 100.

Replication Control

The replication control to be performed by the storage system 400 according to the present embodiment will now be described. Replication control is performed by the CPU 211 of the disk control unit 210 executing the replication control program 217. The storage volume 230 to be the target of replication and the control type of replication are defined in the pair management table 216. The pair management table 216 can be created based on the data, which is input from the input unit 150 by the operator who operates the information unit 100, when the storage management program 193 is executed in the information processing unit 100, for example. If the storage management program 193 is provided to the management console 260, and the CPU 261 of the management console 260 can execute the storage management program 193, then the pair management table. 216 can be created based on the data which is input from the input unit 265 by an operator who operates the management console 260.

FIG. 4 shows the pair management table 216. The pair management table 216 is comprised of the "pair type" column, "replication type" column, "replication source unit" column, "replication destination unit" column, "replication source volume" column, "replication destination volume" column and "pair status" column.

A pair refers to a combination of storage volumes 230 created by the two storage volumes 230. The two storage volumes 230 forming a pair, which are in a same storage unit 200, are referred to as "a local pair", those which are in a different storage unit 200 are referred to as "a remote pair". In the storage volumes 230 forming a pair, one is managed as a main storage volume 230, and the other is managed as a sub-storage volume 230. When data is written to the main storage volume 230, the replication of the data is written to the sub-storage volume 230. For one main storage volume 230, a plurality of sub-storage volumes 230 may be combined.

When the information processing unit 200 for executing the storage management program 193 instructs the storage unit A (200), which is the data replication source, to create a remote pair, the storage unit A (200) updates the pair management table 216. Then the storage unit A (200) instructs the storage unit B (200), which is the data replication destination, to create a remote pair. And the storage unit B (200) updates the pair management table 216 of the memory 212 in the storage unit B (200).

The "pair type" column of the pair management table 216 shows whether this pair is a local pair or remote pair. The "replication type" column shows whether the type of replication is synchronous or asynchronous when this pair is a remote pair. The "replication source unit" column and the replication destinations column show the storage unit 200 at the replication source and the storage unit 200 at the replication destination when this pair is a remote pair. The "replication source volume" column shows the identification number of the main storage volume 230 of this pair, and the "replication destination volume" column shows the identification number of the sub-storage volume 230 of this pair. For the identification number of the storage volume 230, a LUN (Logical Unit number), for example, can be used.

The "pair status" column shows the status of this pair. The pair status is "pair", "split" or "re-sync". In the case of "pair", the replication of data written from the information processing unit 100 to the main storage volume 230 is also written to the sub-storage volume 230. By this, the correspondence of the main storage volume 230 and the sub-storage volume 230, the sameness of the content stored in the main storage volume 230 and the content in the sub-storage volume 230, can be assured.

In the case of "split", data written from the information processing unit 100 to the main storage volume 230 is not reflected on the sub-storage volume 230. "re-sync" is a transient status from "split" to "pair". In other words, this is a status when the update data in the main storage volume 230 during "split" is being reflected on the sub-storage volume 230. When the reflection completes, the status of this pair becomes "pair".

The above mentioned pair creation, pair split and pair re-sync can be executed by an operator sending the instructions via the input unit 150 to the information processing unit 100 where the storage control program 193 is executed. The instruction input from the operator is sent to the disk control unit 210. The disk control unit 210 executes the replication control program 217, and changes pair formation and pair status according to the above instructions. When the data write request for the main storage volume 230 in "pair" status is received from the information processing unit 100, for example, the disk control unit 210 writes the data to the main storage volume 230 according to the pair status of the formed pair, specifies the storage volume B 230 to which the replication of the data is written referring to the pair management table 216, and sends the replication of this data to the storage unit B (200). And the storage unit B (200) receives the replication of this data, and writes the replication of this data to the storage volume B 230.

By the above replication control, the data of the computer system at the main system can be stored in the computer system in the remote site.

Cluster Control

The cluster control to be performed by the storage system 400 according to the present embodiment will now be described.

The information processing unit A (100) and the information processing unit B (100) according to the present embodiment perform cluster control 196 by executing the clustering control program for each other. Cluster control is a control for the computer system at the remote site to take over the information processing which the computer system at the main site has been performing when the computer system at the remote site detects a shut down of the computer system at the main site. Taking over the information processing is also called "fail-over".

In this case, when the computer system at the remote site detects a shut down of the computer system at the main site, the computer system at the main site normally repeatedly sends predetermined data called "heart beat signals" (heart beat message) to the computer system at the remote site at intervals within a predetermined time. The computer system at the remote site can judge the operation status of the computer system at the main site by detecting the heart beat signal sent from the computer system at the main site. For example, when the computer system at the remote site cannot detect the heart beat signal from the computer system at the main site after waiting a predetermined time, the computer system at the remote site can judge that an abnormality occurred to the computer system at the main site.

Transmission/Reception of Heart Beat Signal

The transmission/reception control of the heart beat signals to be performed in the storage system 400 according to the present embodiment will be described with reference to FIG. 5 to FIG. 14.

FIG. 5 shows a system block diagram depicting the transmission/reception control of the heart beat signals according to the present embodiment. The difference from the system block diagram in FIG. 1 is that a plurality of information processing units 100 are in the main site and the remote site respectively in the system block diagram in FIG. 5. In this case, cluster control can be performed in an information processing unit A (100) in the main site by transmitting/receiving heart beat signals with another information processing unit A (100) in the main site, for example. In other words, when an information processing unit A (100) in the main site detects that another information processing unit A (100) in the main site stopped operation, the former information processing unit A (100) in the main site can take over the information processing which the failed information processing unit A (100) has been performing. This is the same for the information processing unit B (100) at the remote site.

The "micro control VOL (VOLume)", "heart beat PVOL (Primary VOLume)", "user PVOL", "heart beat SVOL (Secondary VOLume)" and "user SVOL" are storage volumes 230 respectively. The micro control VOL (230) is a storage volume 230 which is used when the transmission/reception of the heart beat signals according to the present embodiment is controlled. In the micro control VOL (230), the heart beat status table 194 is stored. Details will be described later.

The heart beat PVOL (230) and the heart beat SVOL (230) constitute a pair in replication, and are the main storage volume 230 and the sub-storage volume 230 respectively. In the heart beat PVOL (230), the heart beat signals 232 are written. Then the replication of the heart beat signal 232 is written to the heart beat SVOL (230) which constitute the pair.

The user PVOL (230) and the user SVOL (230) constitute a pair in replication, and are the main storage volume 230 and the sub-storage volume 230 respectively. In the user PVOL (230), various data, which is generated by the application program 190 being executed in the information processing unit 100, is written. Then the replication of the data is written to the user SVOL (230) constituting the pair.

In the transmission/reception of the heart beat signals 232 according to the present embodiment, the heart beat control program 191 and the node heart beat control program 192 are executed by the information processing unit 100 under the control of the operating system 197, and the disk heart beat control program 215, storage control program 218 and replication control program 217 are executed by the storage unit 200.

The operating system 197 provides an API (Application Program Interface) when various programs, such as the heart beat control program 191, are executed by the information processing unit 100. For example, the operating system 197 provides "OPEN", "READ", "WRITE" and "CLOSE" for the storage volume 230. In this case, if the node heart beat control program 192 writes the heart beat signal 232 to the heart beat PVOL (230) of the storage unit 200, for example, "OPEN" is used when the pointer to the heart beat PVOL (230) is acquired, "WRITE" is used when the heart beat signal 232 is written, and "CLOSE" is used when the pointer to the heart beat PVOL (230) is relinquished. If the node heart beat control program 192 reads the heart beat signal 232 from the heart beat SVOL (230) of the storage unit 200, "OPEN" is used when the pointer to the heart beat SVOL (230) is acquired, "READ" is used when the heart beat signal 232 is read, and "CLOSE" is used when the pointer to the heart beat SVOL (230) is relinquished.

The heart beat control program 191 creates and updates the activation/deactivation message 195 and the heart beat status table 194 which are stored in the memory 120 of the information processing unit 100, and creates and updates the heart beat status table 194 which is stored in the micro control volume 230 of the storage unit 200. The activation/deactivation message 195 is created and updated based on the data which is input by the operator from the input unit 150 of the information processing unit 100, for example. The heart beat status table 194 can be created and updated based on the content of the activation/deactivation message 195, for example. The heart beat control program 191, which is executed by the information processing unit 100 at the remote site, judges the operation status of the computer system at the main site according to the detection result of the heart beat signal 232, which is sent from the computer system at the main site. Details will be described later.

The node heart beat control program 192 repeatedly sends a request to write the heart beat signals (second heart beat message, hereafter also called "node heart beat signal 232") 232 to the heart beat PVOL (230), to the storage unit 200 at intervals within a predetermined time based on the heart beat status table 194 stored in the memory 120. This node heart beat signal 232 is written to the heart beat PVOL (230) by the storage unit 200. The node heart beat control program 192 also sends a request to read the replication of the node heart beat signal 232 written in the heart beat SVOL (230) to the storage unit 200 based on the heart beat status table 194 stored in the memory 120. The replication of this node heart beat signal 232 is read from the heart beat SVOL (230) by the storage unit 200, and sent to the information processing unit 100. And the node heart beat control program 192 detects the replication of the node heart beat signal 232 which is transmitted from the storage unit 200. And the node heart beat control program 192 updates the content of the heart beat status table 194 of the memory 120. Details will be described later.

The disk heart beat control program 215 repeatedly writes the heart beat signals (first heart beat message, hereafter also called "disk heart beat signal 232" 232 to the heart beat PVOL (230) at intervals within a predetermined time based on the heart beat status table 194 stored in the micro control VOL (230). Here the heart beat PVOL (230), to which the disk heart beat signal 232 is written by the disk heart beat control program 215, may be the same storage volume 230 as the heart beat PVOL (230) to which the node heart beat signal 232, which is transmitted by the node heart beat control program 192, is written, or may be a different storage volume 230. The disk heart beat control program 215 also reads the replication of the disk heart beat signal 232, which is written in the heart beat SVOL (230) based on the heart beat status table 194 stored in the micro control VOL (230), and detects the replication. And the disk heart beat control program 215 updates the content of the heart beat status table 194 stored in the micro control VOL (230). Details will be described later.

When the heart beat signal 232 is written to the heart beat PVOL (230), the replication control program 217 sends the replication of the heart beat signal 232 to the storage unit 200 at the remote site via the second network 310, based on the pair management table 216. The replication control program 217 receives the replication of the heart beat signal 232 which is sent from the storage unit 200 at the main site via the second network 310, and writes the replication of the heart beat signal 232 to the heart beat SVOL (230).

The storage control program 218 writes the node heart beat signal 232 to the heart beat PVOL (230) according to the write request of the heart beat signal 232, which is sent from the information processing unit 100. The storage control program 218 also reads the replication of the node heart beat signal 232 from the heart beat SVOL (230) according to the read request of the replication of the node heart beat signal 232 which is sent from the information processing unit 100, and sends the replication to the information processing unit 100. The storage control program 218 also sends the replication detection result of the disk heart beat signal 232 to the information processing unit 100.

Activation/Deactivation Message

FIG. 6 shows the activation/deactivation message 195 according to the present embodiment. As described above, the activation/deactivation message 195 is created based on the data which is input by the operator from the input unit 150 of the information processing unit 100 at the main site. The activation/deactivation message 195 is created each time an operator inputs data. In other words, an operator can transmit/receive any number of types of heart beat signals 232 between the computer system at the main site and the computer system at the remote site.

The activation/deactivation message 195 is comprised of the "activation/deactivation type" column, "disk heart beat/node heart beat type" column, "local device address" column and "remote device address" column.

The "activation/deactivation type" column shows the enabling/disabling transmission/reception of the heart beat signal 232. Enabling transmission/reception of the heart beat signal 232 is referred to as activating the heart beat signal 232. Disabling transmission/reception of the heart beat signal 232 is referred to as deactivating the heart beat signal 232. The values to be written in the "activation/deactivation type" column can be "ACTIVATE" and "DEACTIVATE", for example. "ACTIVATE" indicates that the heart beat signal 232 is activated, and "DEACTIVATE" indicates that the heart beat signal 232 is deactivated.

The "disk heart beat/node heart beat type" column shows whether the heart beat signal 232 to be activated or deactivated is the node heart beat signal 232 or the disk heart beat signal. The value to be written in the "disk heart beat/node heart beat type" column can be "DISK HEART BEAT" or "NODE HEART BEAT", for example. "DISK HEART BEAT" indicates that the heart beat signal 232 to be activated or deactivated is the disk heart beat signal 232, and "NODE HEART BEAT" indicates that the heart beat signal 232 to be activated or deactivated is the node heart beat signal 232.

The "local device address" column shows the address (storage position) of the heart beat PVOL (230) to which the heart beat signal 232 is written.

The "remote device address" column shows the address (storage position) of the heart beat SVOL (230) to which the heart beat signal 232 is written.

The heart beat control program 191 sends the activation/deactivation message 195 created based on the data which is input by an operator to the information processing unit 100 at the remote site. The activation/deactivation message 195 may be transmitted to the information processing unit 100 of the remote site via the first network 300 or via the second network 310. To transmit via the second network 310, replication may be used for the transmission.

Heart Beat Status Table

Then the information processing unit 100 at the main site and the information processing unit 100 at the remote site create and update the heart beat status table 194 based on the activation/deactivation message 195 respectively. FIG. 7 shows the heart beat status table according to the present embodiment.

The heart beat status table 194 is comprised of a portion which shows the status of the node heart beat signal 232 and the portion showing the status of the disk heart beat signal 232.

The portion showing the status of the node heart beat signal 232 is comprised of the "node heart beat status" column, "P/S type" column, "local device address" column, "remote device address" column and "device status" column. One or more "P/S type" columns, "local device address" columns, "remote device address" columns and "device status" columns are created for the number of types of the node heart beat signals 232. In other words, the types of the node heart beat signal 232 are specified by the combination of the "P/S type" column, "local device address" column and "remote device address" column.

The "node heart beat status" column shows whether the node heart beat signal 232 is transmitted/received between the computer system at the main site and the computer system at the remote site. The value to be written in the "node heart beat status" column can be "ENABLE" or "FAILED". "ENABLE" indicates that at least one type of node heart beat signal 232 is being transmitted/received between the computer system at the main site and the computer system at the remote site. "FAILED" indicates that the node heart beat signal 232 is not transmitted/received at all.

The "P/S type" column shows whether the node heart beat signal 232 is to be transmitted or received. In other words, the "P/S type" column indicates whether the next column, "local device address" is the heart beat PVOL (230) or the heart beat SVOL (230). The value to be written in the "P/S type" column can be "PVOL" or "SVOL". The information processing unit 100, which created the activation/deactivation message 195, sets "PVOL" in the "P/S type" column. The information processing unit 100, to which the activation/deactivation message 195 is transmitted, sets "SVOL" in the "P/S type" column.

The "local device address" column shows an address where the node heart beat signal 232 is written in the storage volume 230 of the storage unit 200 in a same computer system. If the "P/S type" column is "PVOL", the node heart beat signal 232, which is written at the address indicated in the "local device address" column, is sent to another storage unit 200 by the replication control program 217. If the "P/S type" column is "SVOL", the node heart beat signal 232, which is sent from another storage unit 200 by the replication control program 217, is written at the address indicated in the "local device address" column.

The "remote device address" column shows an address where the node heart beat signal 232 is written in the storage volume 230 of the storage unit 200 in a different computer system.

The "device status" column shows whether the node heart beat signal 232 is transmitted/received correctly. The value to be written in the "device status" column can be "ENABLE" or "FAILED". "ENABLE" indicates that the node heart beat signal 231 is being correctly transmitted/received. "FAILED" indicates that the node heart beat signal 232 is not being correctly transmitted/received.

If the "device status" column is "FAILED" for all types of node heart beat signals 232, this means that the transmission/reception of the node heart beat signal 232 is all incorrect, so "FAILED" is written in the "node heart beat status" column.

How to decide whether the node heart beat signal 232 is correctly transmitted/received or not will be described later.

The portion indicating the status of the disk heart beat signal 232 is comprised of the "disk heart beat status" column, "P/S type" column, "local device address" column, "remote device address" column and "device status" column. One or more "P/S type" columns, "local device address" columns, "remote device address" columns and "device status" columns are created for the number of types of the disk heart beat signals 232. In other words, the types of the disk heart beat signals 232 are specified by the combination of the "P/S type" column, "local device address" column and "remote device address" column.

The "disk heart beat status" column shows whether the disk heart beat signal 232 is being transmitted/received between the computer system at the main site and the computer system at the remote site. The value to be written in the "disk heart beat status" can be "ENABLE" or "FAILED". "ENABLE" indicates that at least one type of the disk heart beat signals 232 is being transmitted/received between the computer system at the main site and the computer system at the remote site. "FAILED" indicates that the disk heart beat signals 232 are not transmitted/received at all.

The "P/S type" column, "local device address" column, "remote device address" column and "device status" column are the same as the portion indicating the status of the node heart beat signal 232.

The heart beat status table 194 to be stored in the micro control VOL (230) may have only the portion indicating the status of the disk heart beat signal 232. By this, the status of the disk heart beat signal 232 can be managed with less storage capacity.

Heart Beat Signal

The node heart beat control program 192 creates the node heart beat signal 232 and repeatedly sends a request to write the node heart beat signal 232 to the heart beat PVOL (230), to the storage unit 200 at intervals within a predetermined time, such as intervals within one minute, based on the heart beat status table 194 stored in the memory 120. The node heart beat signal 232 is written in the heart beat PVOL (230) by the storage control program 218, which is executed by the storage unit 200.

The disk heart beat control program 215 creates the disk heart beat signal 232, and repeatedly writes the disk heart beat signal 232 to the heart beat PVOL (230) at intervals within a predetermined time, such as intervals within one minute, based on the heart beat status table 194 stored in the micro control VOL (230).

Figure 8:
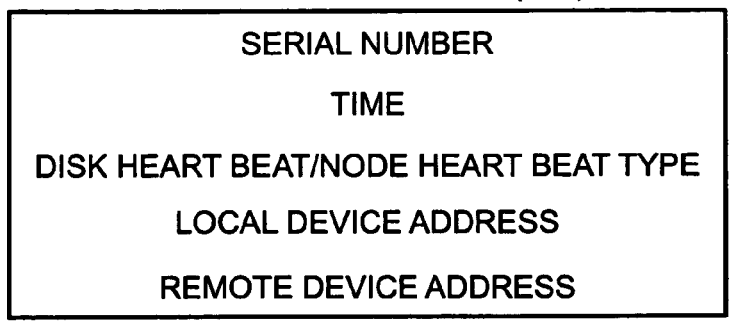
FIG. 8 is a diagram showing a heart beat signal according to the present embodiment.
Figure 9:
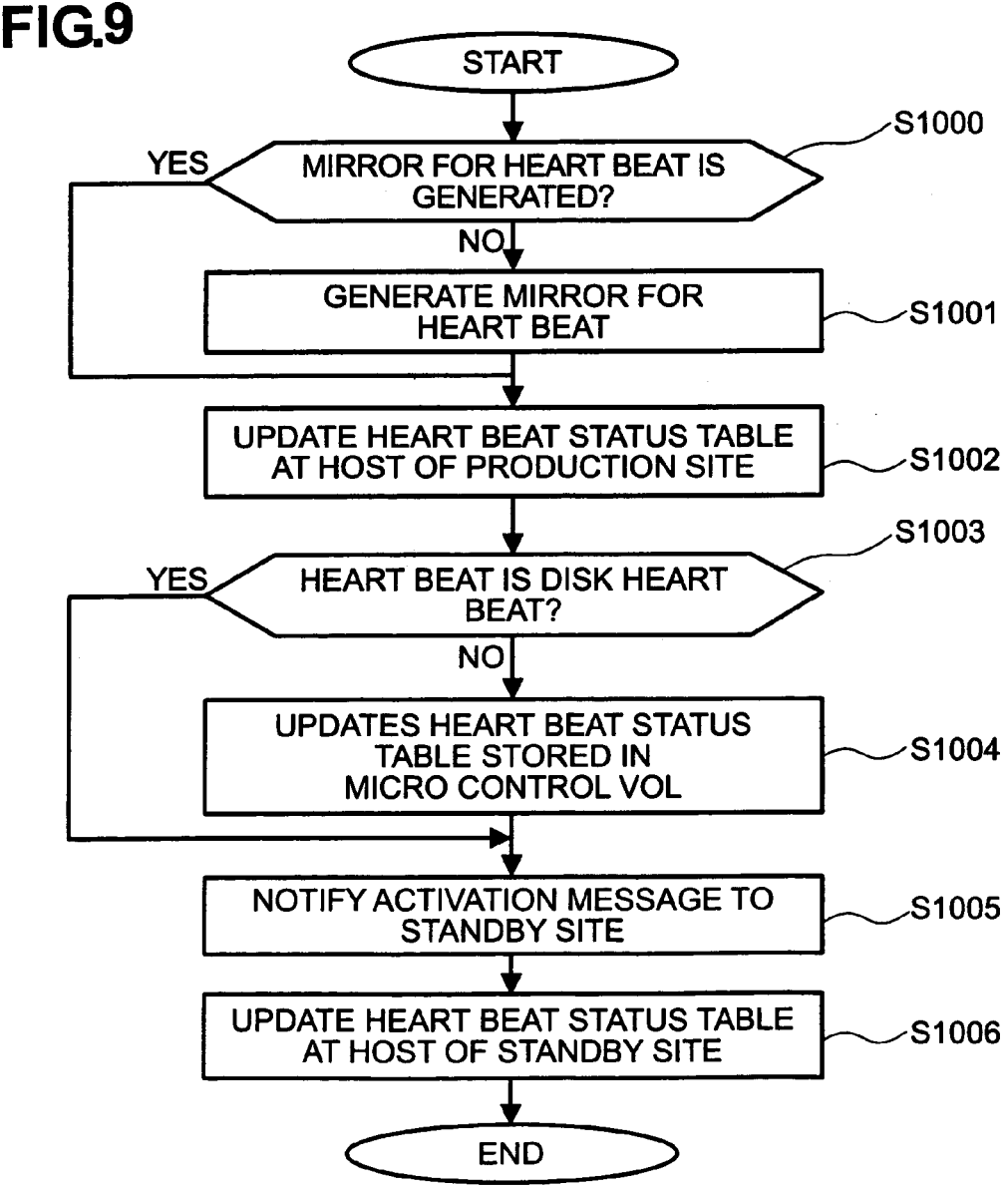
FIG. 9 is a flow chart depicting the flow of activation processing of a heart beat signal according to the present invention.

FIG. 8 shows the node heart beat signal 232 and the disk heart beat signal 232 according to the present embodiment. As FIG. 8 shows, the node heart beat signal 232 and the disk heart beat signal 232 according to the present embodiment, is comprised of at least one of "serial number" column, "time" column, "disk heart beat/node heartbeat type" column, "local device address" column and "remote device address" column.

The "serial number" column is a column where the identification information for identifying each one of a same type of heart beat signals 232 which are written in the heart beat PVOL (230) at intervals within a predetermined time.

The serial number can be a number which is incremented by 1 each time the heart beat signal 232, which is sequentially written to the heart beat. PVOL (230), is written.

The "time" column is a column where information indicating the time when the heart beat signal 232 was created, by the node heart beat control program 192 or the disk heart beat control program 215, is written. Time can be the date and time when the heart beat signal 232 was created, or can be information indicating the difference from a predetermined reference date and time.

The "disk heart beat/node heart beat type" column is a column where information, indicating whether the signal is the node heart beat signal 232 created by the node heart beat control program 192 or the disk heart beat signal 232 created by the disk heart beat control program 215, is written.

The "local device address" column is a column where the information indicating the storage position of the heart beat PVOL (230), to which the heart beat signal 232 is written, is written. The "remote device address" column is a column where the information indicating the storage position of the heart beat SVOL (230), to which the heart beat signal 232 is written, is written.

Checking Correct Transmission/Reception of Node Heart Beat Signal

The node heart beat control program 192, to be executed in the information processing unit 100 at the remote site, refers to the heart beat status table 194, and for the devices of which the "P/S type" column is "SVOL" and the "device status" column is "ENABLE", the node heart beat control program 192 specifies the address written in the "local device address" column respectively, and sends a request to read the replication of the node heart beat signal 232 to the storage unit 200. This read request can be sent at every predetermined time, such as at one minute intervals. The replication of this node heart beat signal 232 is read from the heart beat SVOL (230) by the storage unit 200, and is sent to the information processing unit 100. And the node heart beat control program 192 judges whether the node heart beat signal 232 is being transmitted/received correctly by comparing the content of the replication of the node heart beat signal 232 which is read from the heart beat SVOL (230) and the content corresponding to the node heart. beat signal 232 in the heart beat status table 194.

Specifically, it is compared whether the content written in the "remote device address" column of the node heart beat signal 232 matches with the content written in the "remote device address" column corresponding to the node heart beat signal 232 in the heart beat status table 194, whether the content written in the "local device address" column in the node heart beat signal 232 matches with the content written in the "local device address" column corresponding to the node heart beat signal 232 in the heart beat status table 194, and whether the content written in the "disk heart beat/node heart beat type" column of the node heart beat signal 232 is "NODE HEART BEAT". Also it is checked that the value written in the "serial number" column of the node heart beat signal 232 is increased from the value of the node heart beat signal 232 received the last time.

The node heart beat control program 192 decides that the node heart beat signal 232 is being transmitted/received correctly when the node heart beat signal 232 matches the contents written in each of the above mentioned columns of the heart beat status table 194, and the content written in the "disk heart beat/node heart beat type" column of the node heart beat signal 232 is "NODE HEART BEAT", and the value written in the "serial number" column of the node heart beat signal 231 is increased from the value of the node heart beat signal 232 received the last time.

According to the decision on whether the node heart beat signal 232 is being transmitted/received correctly, the node heart beat control program 192 writes "ENABLE" or "FAILED" in the "device status" column of the heart beat status table 194.

The node heart beat control program 192 writes "FAILED" in the "node heart beat status" column when the "device status" column is all "FAILED" for the portion indicating the status of the node heart beat signal 232 of the heart beat status table 194.

Checking Correct Transmission/Reception of Disk Heart Beat Signal

The disk heart beat control program 215 refers to the heart beat status table 194 stored in the micro control VOL (230), and for the devices of which the "P/S type" columns is "SVOL" and the "device status" column is "ENABLE", the disk heart beat control program 215 reads the replication of the heart beat signal 232 from the heart beat SVOL (230) written in the "local device address" column respectively. This reading can be executed at every predetermined time, such as at one minute intervals. The disk heart beat control program 215 judges whether the disk heart beat signal is being transmitted/received correctly by comparing the content of the replication of the disk heart beat signal 232 that is read from the heart beat SVOL (230), and the content corresponding to the disk heart beat signal 232 in the heart beat status table 194.

Specifically, it is compared whether the content written in the "remote device address" column of the disk heart beat signal 232 matches with the content written in the "remote device address" column corresponding to the disk heart beat signal 232 in the heart beat status table 194, whether the content written in the "local device address" column of the disk heart beat signal 232 matches with the content written in the "local device address" column corresponding to the disk heart beat signal 232 in the heart beat status table 194, and whether the content written in the "disk heart beat/node heart beat type" column of the disk heart beat signal 232 is "DISK HEART BEAT". Also it is checked that the value written in the "serial number" column of the disk heart beat signal 232 is increased from the value of the disk heart beat signal 232 received the last time.

The disk heart beat control program 192 decides that the disk heart beat signal 232 is being transmitted/received correctly when the disk heart beat signal 232 matches with the content written in each of the above mentioned columns of the heart beat status table 194, and the content written in the "disk heart beat/node heart beat type" column of the disk heart beat signal 232 is "DISK HEART BEAT", and the value written in the "serial number" column of the disk heart beat signal 232 is increased from the value of the disk heart beat signal 232 received the last time.

Then according to the decision on whether the disk heart beat signal 232 is being transmitted/received correctly, the disk heart beat control program 215 writes "ENABLE" or "FAILED" in the "device status" column of the heart beat status table 194.

The disk heart beat control program 215 writes "FAILED" in the "disk heart beat status" column when the "device status" column is all "FAILED" for the portion indicating the status of the disk heart beat signal 232 of the heart beat status table 194.

Judging Operation Status of Computer System at Main Site

The heart beat control program 191 to be executed in the information processing unit 100 at the remote site transmits the read request of the heart beat status table 194 stored in the micro control VOL (230) to the storage unit 200 at the remote site. This read request can be transmitted at every predetermined time, such as at one minute intervals. And the storage unit 200 sends the heart beat status table 194 stored in the micro control VOL (230) to the information processing unit 100. The heart beat control program 191 reflects the portion indicating the status of the disk heart beat signal 232 out of the heart beat status table 194 sent from the storage unit 200 in heart beat status table 194 stored in the memory 120. And the heart beat control program 191 checks whether the node heart beat signal 232 and the disk heart beat signal 232 are being correctly transmitted/received between the computer system at the main site and the computer system at the remote site. By this, the heart beat control program 191 judges the operation status of the computer system at the main site according to the detection result of the replication of the disk heart beat signal 232 and the detection result of the replication of the node heart beat signal 232.

The information processing unit 100 at the remote site also judges whether it is necessary to execute fail-over according to the operation status of the computer system at the main site, and if necessary, the information processing in the computer system at the main site is transferred to the computer system at the remote site. The fail-over can be executed by the clustering control program 196. Details will be described later.

Activation/Deactivation of Heart Beat Signal

Now the processing flow to activate the heart beat signal 232 and the processing flow to deactivate the heart beat signal 232 will be described. At first, the processing flow to activate the heart beat signal 232 will be described with reference to the flow chart shown in FIG. 9.

First, the heart beat control program 191 creates an activation/deactivation message 195 based on the data which an operator input to the input unit 150 of the information processing unit 100 at the main site.

If the instruction from the operator is to activate the heart beat signal 232, the heart beat control program 191 checks whether the mirror for the heart beat has been generated (S1000). The mirror for the heart beat is the heart beat PVOL (230) and the heart beat SVOL (230) where the replication pair is formed. If the mirror for the heart beat is not generated, the mirror for the heart beat is generated (S1001). The mirror for the heart beat may be generated by the replication control program 217.

When the mirror for the heart beat is generated, the heart beat control program 191 updates the heart beat status table 194 stored in the memory 120 of the information processing unit 100 at the main site (S1002). For example, the "node heart beat status" column of the heart beat status table 194 is changed to "ENABLE". The production site which is written in FIG. 9 and other drawings is the main site. The standby site is the remote site.

Then the heart beat control program 191 checks whether an operator instructed activation for the disk heart beat. signal 232 (S1003). If activation is instructed for the disk heart beat signal 232, processing advances to "YES", and the heart beat status table 194 stored in the micro control VOL (230) is updated (S1004). For example, the "disk heart beat status" column of the heart beat status table 194 is changed to "ENABLE".

And the heart beat control program 191 sends the activation/deactivation message 195 to the computer system at the remote site (S1005). The heart beat control program 191 to be executed in the information processing unit 200 of the computer system at the remote site updates the heart beat status table 194 in the computer system at the remote site according to the procedure described above (S1006).

Figure 10:
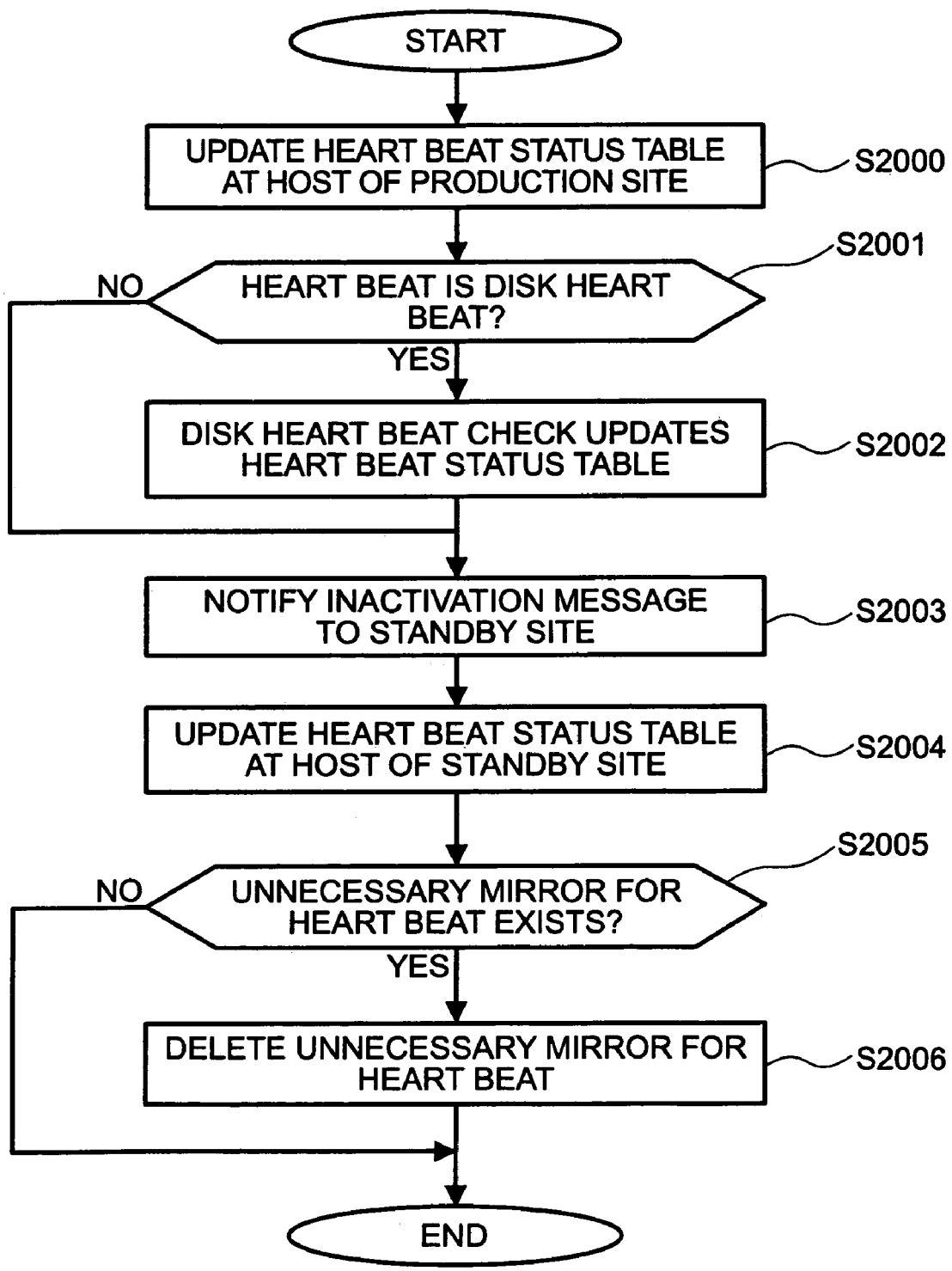
FIG. 10 is a flow chart depicting the flow of deactivation processing of a heart beat signal according to the present embodiment.
Figure 11:
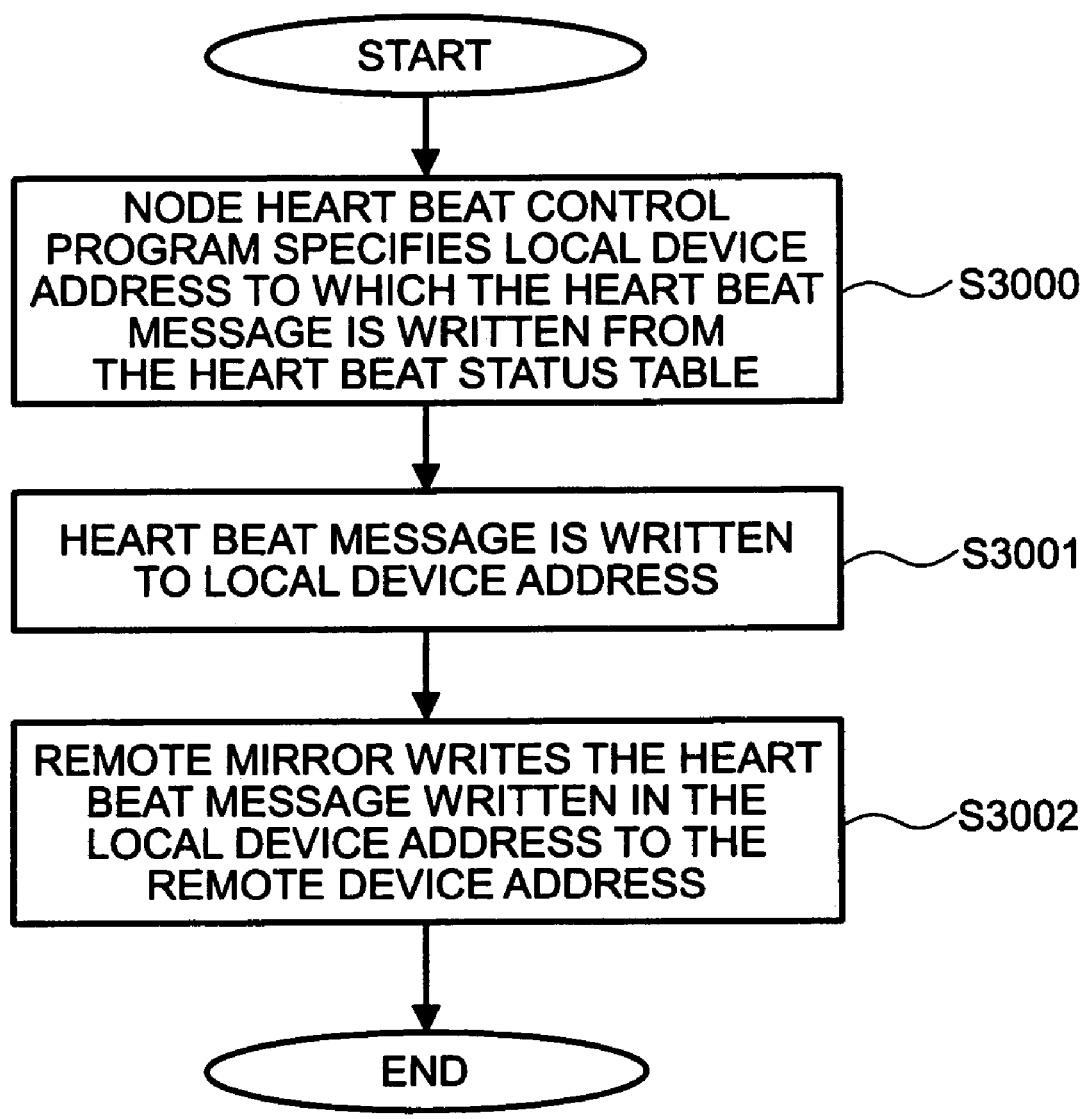
FIG. 11 is a flow chart depicting the flow of transmission processing of a node heart beat signal according to the present embodiment;.
Figure 12:
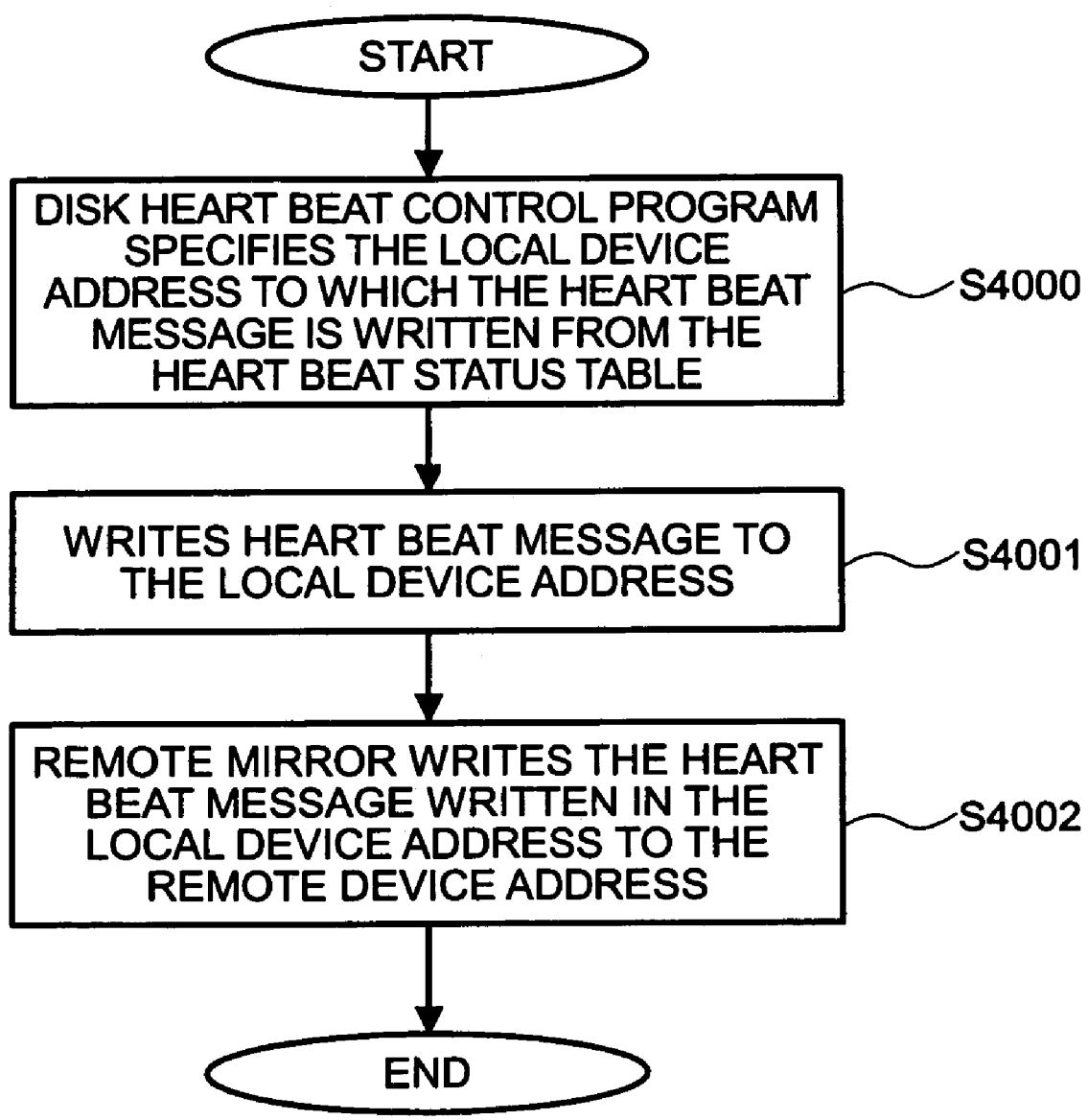
FIG. 12 is a flow chart depicting the flow of transmission processing of a disk heart beat signal according to the present embodiment.

Now the processing flow to deactivate the heart beat signal 232 will be described with reference to the flow chart in FIG. 10.

At first, the heart beat control program 191 creates an activation/deactivation message 195 based on the data which an operator input to the input unit 150 of the information processing unit 100 at the main site.

If the instruction from the operator is to deactivate the heart beat signal 232, the heart beat control program 191 updates the heart beat status table 194 stored in the memory 120 of the information processing unit 100 at the main site (S2000). For example, the "node heart beat status" column of the heart beat status table 194 is changed to "FAILED".

Then the heart beat control program 191 checks whether the operator instructed deactivation for the disk heart beat signal 232 (S2001). If deactivation is instructed for the disk heart beat signal 232, processing advances to "YES", and the heart beat status table 194 stored in the micro control VOL (230) is updated (S2002). For example, the "disk heart beat status" column of the heart beat status table 194 is changed to "FAILED".

And the heart beat control program 191 sends the activation/deactivation message 195 to the computer system at the remote site (S2003). The heart beat control program 191 to be executed in the information processing unit 200 of the computer system at the remote site updates the heart beat status table 194 in the computer system at the remote site according to the procedure described above (S2004).

And the heart beat control program 191 checks whether an unnecessary mirror for the heart beat exists (S2005). If an unnecessary mirror for the heart beat exists, it is deleted (S2006). The unnecessary mirror for the heart beat may be deleted by the replication control program 217.

Transmission of Node Heart Beat Signal

When the node heart beat signal 232 is activated by the above processing, transmission of the node heart beat signals 232 from the computer system at the main site to the computer system at the remote site starts. The processing flow when the node heart beat signal 232 is transmitted will be described with reference to the flow chart in FIG. 11.

At first, the node heart beat control program 192 refers to the portion indicating the status of the node heart beat signal 232 in the heart beat status table 194 stored in the memory 120, and specifies the address of the heartbeat PVOL (230) written in the "local device address" column for the devices of which the "P/S type" column is "PVOL" and the "device status" column is "ENABLE" (S3000). And the node heart beat control program 192 specifies the address of the heart beat PVOL (230), and sends the write request of the node heart beat signal 232 to the storage unit 200. This node heart beat signal 232 is written to the heart beat PVOL (230) by the storage control program 218 which is executed in the storage unit 200 (S3001). And the replication control program 217 sends the node heart beat signal 232 written in the heart beat PVOL (230) to the storage unit 200 at the remote site via the second network 310 based on the pair management table 216. The replication control program 217 writes the node heart beat signal 232 transmitted from the storage unit 200 at the main site to the heart beat SVOL (230) via the second network 310 (S3002). By this, the node heart beat signal 232 can be sent from the computer system at the main site to the computer system at the remote site. The remote mirror written in FIG. 11 and other drawings is the replication control program 217.

The above processing is executed for each device of which the "P/S type" column is "PVOL" and the "device status" column is "ENABLE" in the portion indicating the node heart beat signal 232 status of the heart beat status table 194 stored in the memory 120.

Transmission of Disk Heart Beat Signal

When the disk heart beat signal 232 is activated, the transmission of the disk heart beat signal 232 from the computer at the main site to the computer at the remote site starts. The processing flow when the disk heart beat signal 232 is transmitted will be described with reference to the flow chart in FIG. 12.

At first, the disk heart beat control program 215 refers to the portion indicating the status of the disk heart beat signal 232 out of the heart beat status table 194 stored in the micro control VOL (230), and specifies the address of the heart beat PVOL (230) written in the "local device address" column for the devices of which the "P/S type" column is "PVOL" and the "device status" column is "ENABLE" (S4000). And the disk heart beat control program 215 writes the disk heart beat signal 232 to the address of the heart beat PVOL (230) (S4001). And the replication control program 217 sends the disk heart beat signal 232 written in the heart beat PVOL (230) to the storage unit 200 at the remote site via the second network 310 based on the pair management table 216. The replication control program 217 writes the disk heart beat signal 232 transmitted from the storage unit 200 at the main site to the heart beat SVOL (230) via the second network 310. By this, the disk heart beat signal 232 can be sent from the computer system at the main site to the computer system at the remote site.

The above processing is executed for each device of which the "P/S type" column is "PVOL" and the "device status" column is "ENABLE" in the portion indicating the disk heart beat signal 232 status of the heart beat status table 194 stored in the micro channel VOL (230).

Reception of Disk Heart Beat Signal

Figure 13:
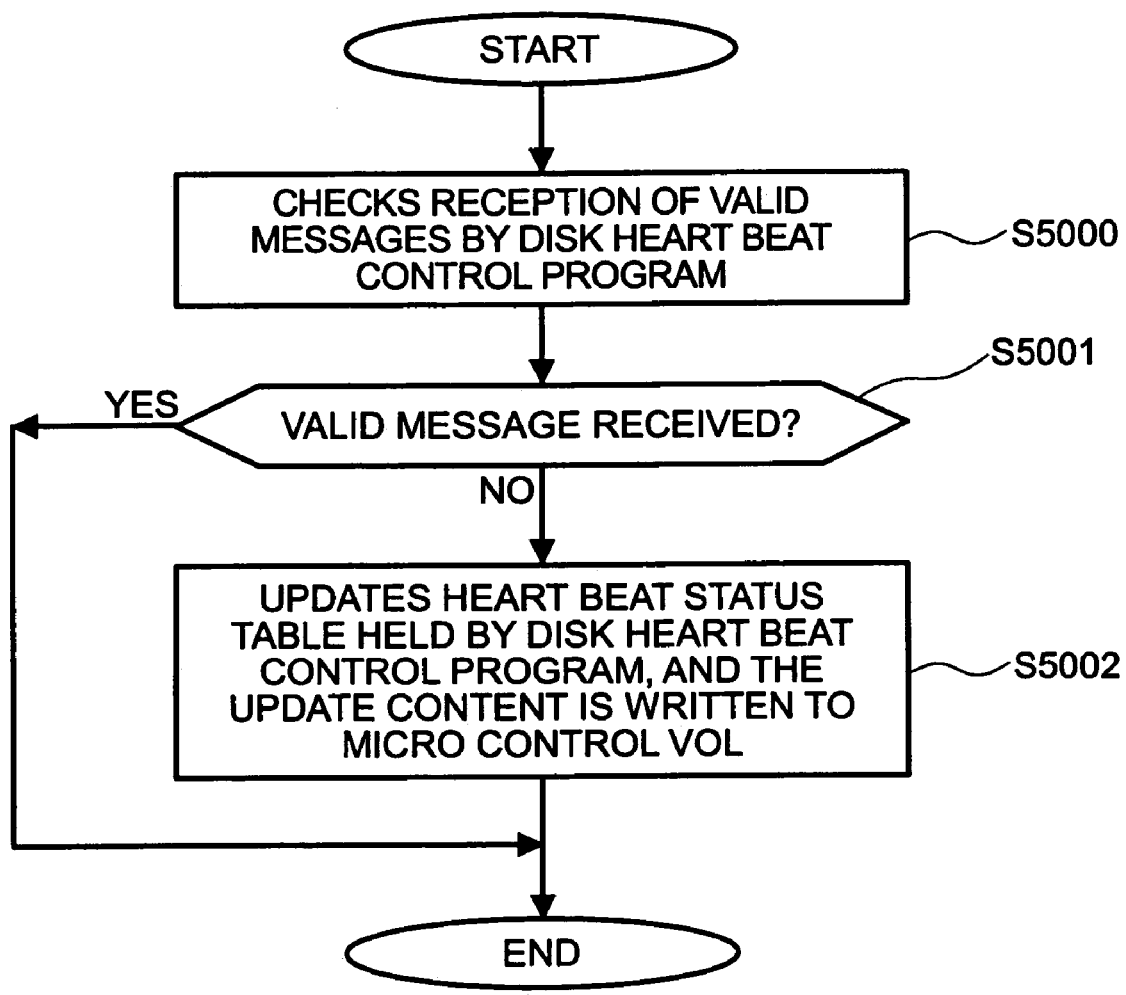
FIG. 13 is a flow chart depicting the flow of reception processing of a disk heart beat signal according to the present embodiment.

The processing flow when the disk heart beat signal 232 is received will now be described with reference to the flow chart shown in FIG. 13.

At first, as described above, the disk heart beat control program 215 compares the content, written in the heart beat status table 194, stored in the micro control VOL (230), and the content of the disk heart beat signal 232 written in the heart beat SVOL (230), and checks whether the disk heart beat signal 232 is normal (S5000). If the disk heart beat signal 232 is abnormal, processing advances to "NO" in S5001, and the content of the heart beat status table 194 stored in the micro control VOL (230) is updated (S5002). This update is executed by writing "FAILED" in the "device status" column of the heart beat status table 194.

Reception of Node Hart Beat Signal

Figure 14:
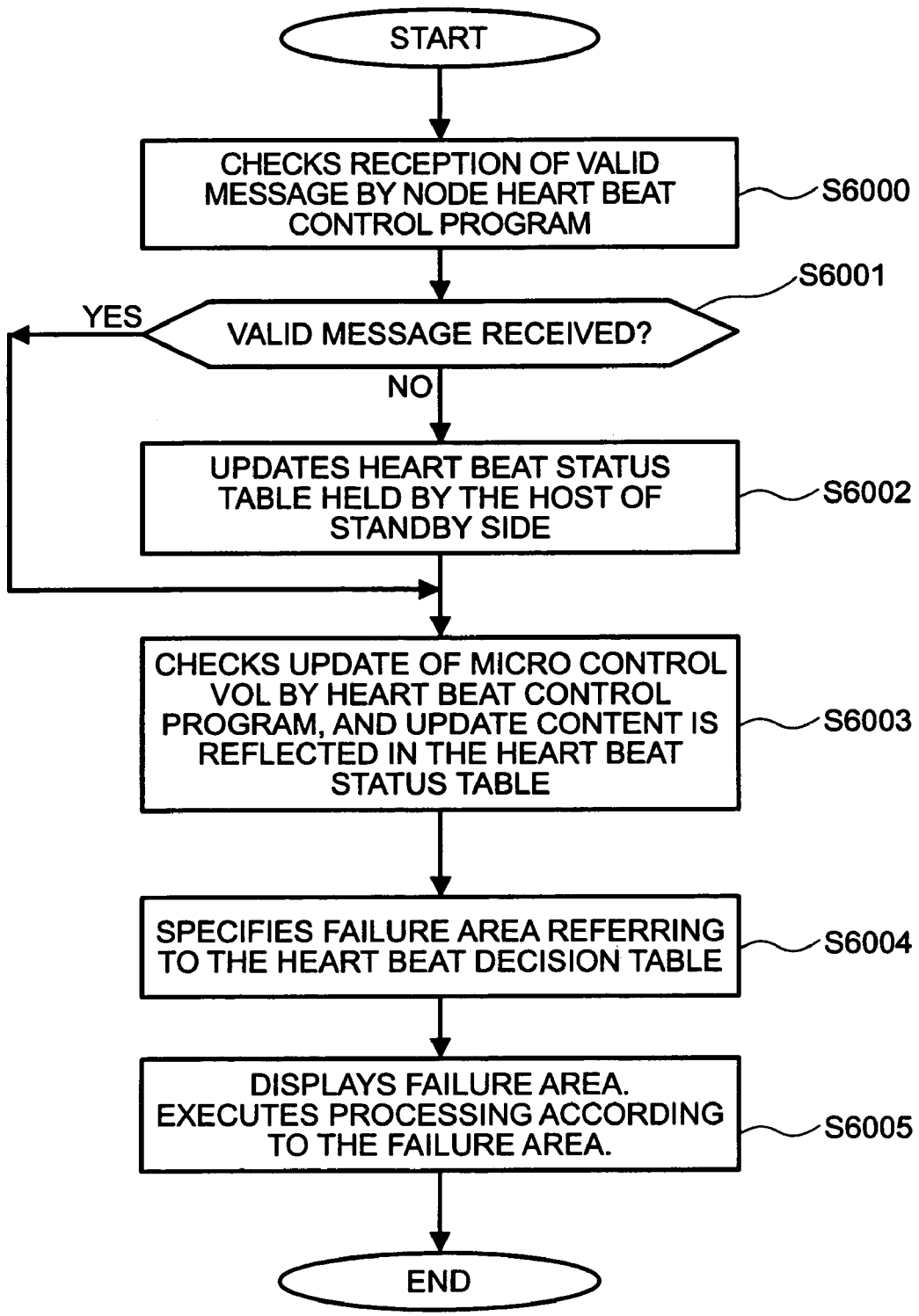
FIG. 14 is a flow chart depicting the flow of reception processing of a node heart beat signal according to the present embodiment.

The processing flow when the node heart beat signal 232 is received will now be described with reference to the flow chart shown in FIG. 14.

At first, as described above, the node heart beat control program 192 sends the request to read the replication of the node heart beat signal 232 written in the heart beat SVOL (230) to the storage unit 200 based on the heart beat status table 194 stored in the memory 120. This replication of the node heart beat signal 232 is read from the heart beat SVOL (230) by the storage control program 218 executed by the storage device 200, and is sent to the information processing unit 100. And the node heart beat control program 192 compares the content written in the heart beat status table 194 stored in the memory 120 and the content of the node heart beat signal 232, and checks whether the node heart beat signal 232 is normal (S6000). If the node heart beat signal 232 is abnormal, processing advances to "NO" in S6001, and the content of the heart beat status table 194 stored in the memory 120 is updated (S6002). This update is executed by writing "FAILED" in the "device status" column of the heart beat status table 194.

The heart beat control program 191, on the other hand, sends the request, to read the heart beat status table 194 stored in the micro control VOL (230), to the storage unit 200. The heart beat control program 191 reflects the portion indicating the status of the disk heart beat signal 232, out of the heart beat status table 194 transmitted by the storage control program 218 which is executed in the storage unit 200, in the heart beat status table 194 stored in the memory 120 (S6003). The heart beat control program 191 judges the operation status of the computer system at the main site, and specifies the failure area (S6004).

Figures 15, 16:
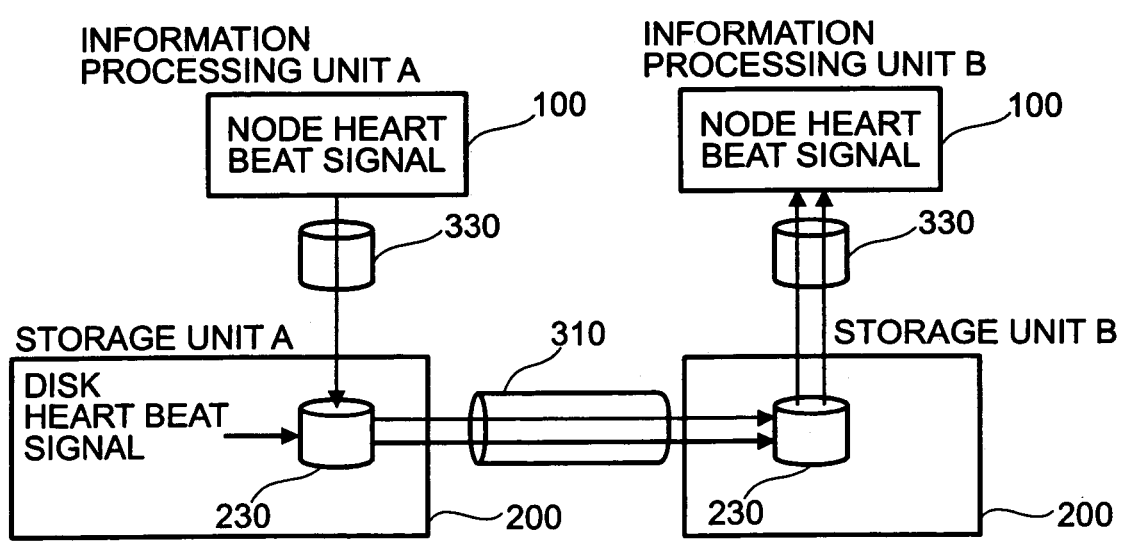
FIG. 15 is a diagram showing a heart beat decision table according to the present embodiment.
FIG. 16 is a block diagram depicting the general configuration of a storage system according to the present embodiment.

The failure area can be specified by referring to the heart beat decision table 198 shown in FIG. 15, for example. In FIG. 15, the node heart beat signal 232 in "OK" is a status where the "node heart beat status" column of the heart beat status table 194 is "ENABLE". The node heart beat signal 232 in "NG" is a status where the "node heart beat status" column of the heart beat status table 194 is "FAILED". This is the same for the disk heart beat signal 232.

Depending on whether the node heart beat signal 232 or the disk heart beat signal 232 was transmitted/received normally, the result is classified into one of "1", "2", "3" and "4" of the heart beat decision table 198, and the failure area is specified.

For example, in the storage system 400 with the configuration shown in FIG. 16, the failure area can be specified as shown in FIG. 17 when the node heart beat signal 232 or the disk heart beat signal 232 is transmitted/received.

FIG. 17 shows that the area indicated by a circle is not abnormal, and the area indicated by a black triangle is potentially abnormal. For example, if the node heart beat signal 232 is transmitted/received normally but the disk heart beat signal 232 is not correctly transmitted/received, for example, this status is classified as "3" in the heart beat decision table 198 in FIG. 15, so it is immediately decided that the disk control unit 210 of the storage unit 200 at the main site is abnormal. If the disk heart beat signal 232 is correctly transmitted/received, but the node heart beat signal 232 is not correctly received, for example, this status is classified as "2" in the heart beat decision table 198 in FIG. 15, so it is immediately decided that the information processing unit 100 at the main site is abnormal, or the input/output path 330 connecting the information processing unit 100 and the storage unit 200 at the main site is abnormal.

Figure 18:
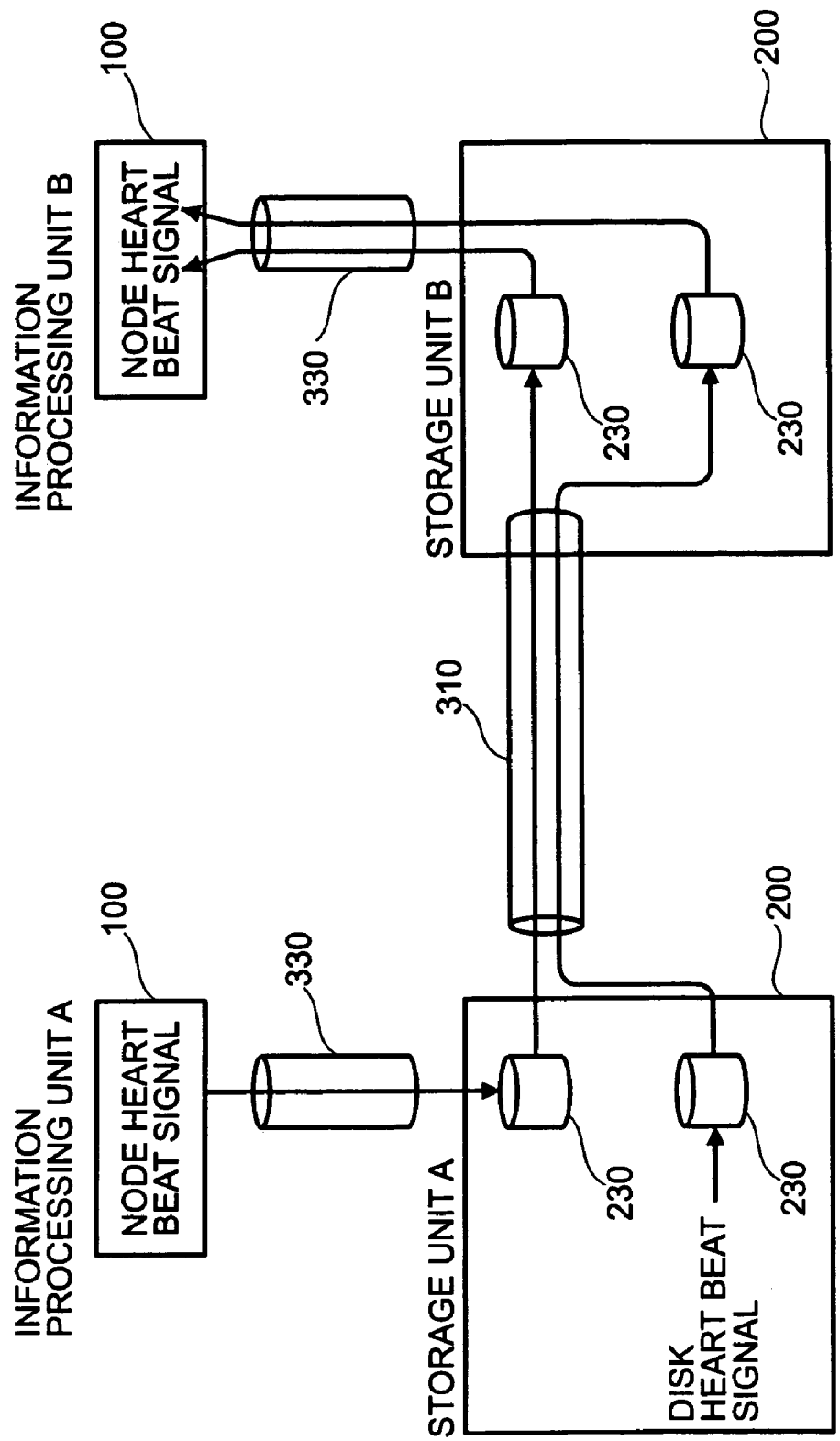
FIG. 18 is a block diagram depicting the general configuration of a storage system according to the present embodiment.

Also in the storage system 400 with the configuration shown in FIG. 18, the failure areas can be specified in detail, as shown in FIG. 19.

Figure 20:
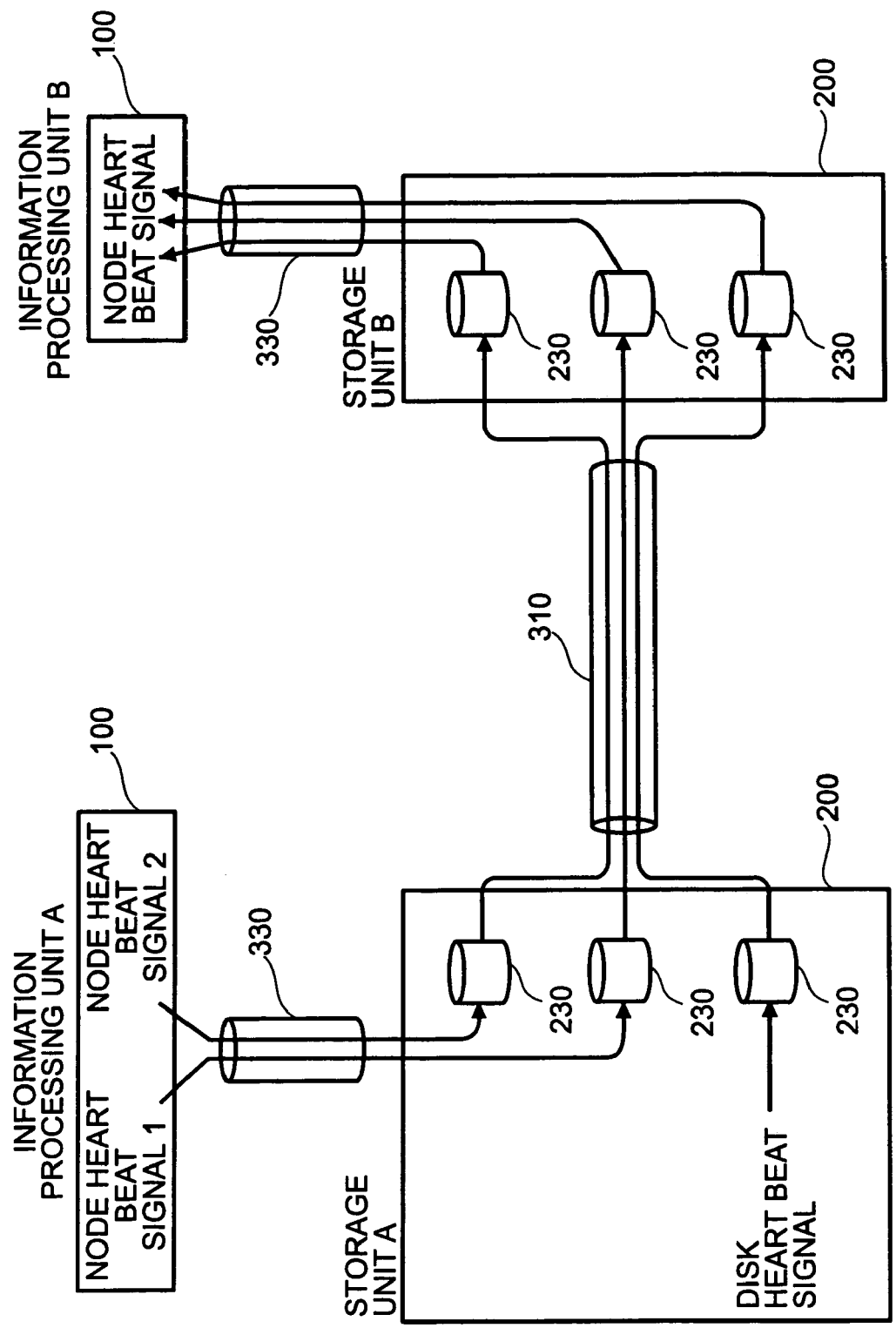
FIG. 20 is a block diagram depicting the general configuration of a storage system according to the present embodiment.
Figure 23:
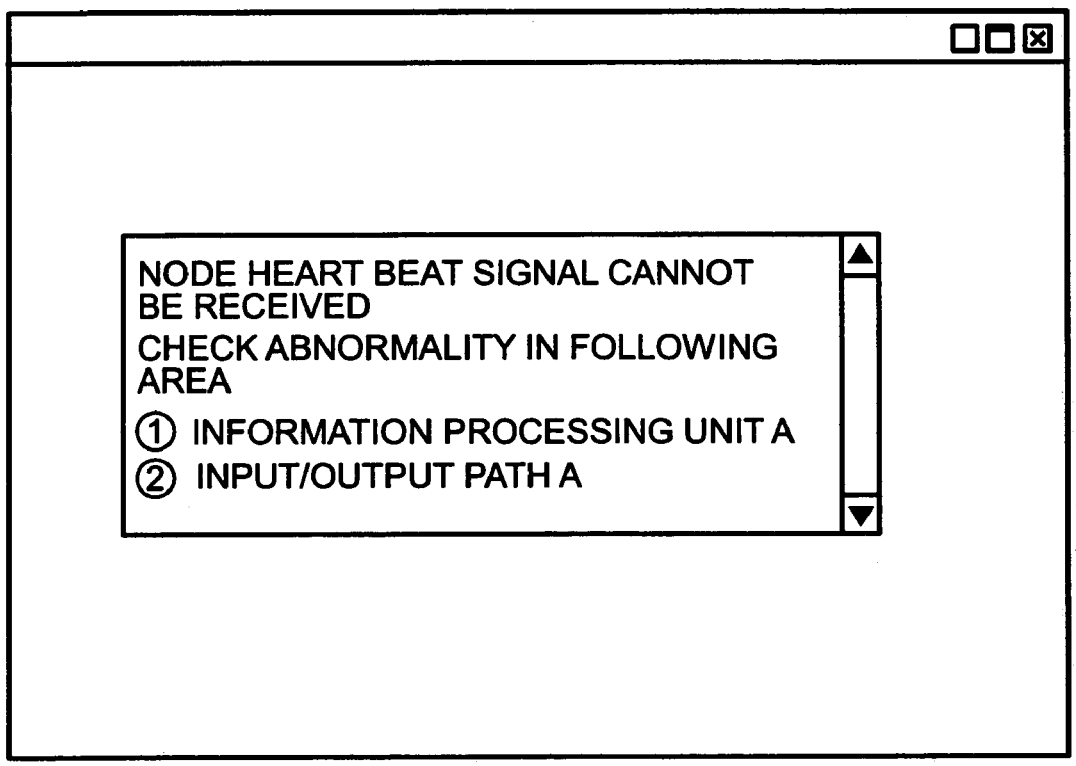
FIG. 23 is a diagram depicting the status when the operation status of the computer system is output to a user interface according to the present embodiment.

If a plurality of node heart beat signals 232 are transmitted/received as shown in FIG. 20, the failure area can be specified in even more detail. The heart beat decision table 198 in this case is as shown in FIG. 21. And depending on whether the node heart beat signal 232 and the disk heart beat signal 232 were transmitted/received normally respectively, the result is classified into one of "1" to "8" in the heart beat decision table 198, and the failure area can be specified in detail.

When the failure area is specified as above, the heart beat control program 191 outputs the operation status of the computer system at the main site to the user interface. And the heart beat control program 191 executes processing according to the failure area (S6005). The operation status can be output through the window which is displayed on the screen of the display, that is the output unit 160 of the information processing unit 100. The output unit 266 of the management console 260 may also be implemented through the window which is displayed on the screen of the display. In the storage system 400 of the present embodiment, the failure area is immediately specified and is output to the user interface, so the failure area can be quickly specified, burden on maintenance and management can be decreased, and the reliability of the computer system can be improved.

The heart beat control program 191 can decide whether a fail over is executed according to the failure area, for example, and can have the clustering control program 196 executes a fail over if necessary. For example, in the configuration of the storage system 400 shown in FIG. 20, if the disk heart beat signal 232 is correctly transmitted/received but the two node heart beat signals 232 are not transmitted/received normally for either case, then whether an abnormality occurred at an area indicated by a black triangle is checked one by one by executing a diagnostic program, and a fail over is performed when it is finally decided that an abnormality occurred to the information processing unit 200 at the main site.

In this way, according to the storage system 400 of the present embodiment, the computer system at the remote site can detect the occurrence of an abnormality to the storage unit 200 at the main site by detecting that the disk heart beat signal 232 is not transmitted from the computer system at the main site. By this, an abnormality of the storage unit 200 at the main site can be detected and specified more quickly. This makes it possible to handle a failure quickly, decrease the burden of maintenance and management, improve the maintenance service, and improve the reliability of the computer system.

In the storage system 400 according to the present embodiment, the transmission/reception of the node heart beat signal 232 is combined in addition to the transmission/reception of the disk heart beat signal 232, so it is possible to specify the failure area of the computer system more easily, in more detail, and more accurately. Also when cluster control is performed, the operation when failure is detected can be specified. For example, when the "node heart beat status" of the heart beat status table 194 is "FAILED" and the "disk heart beat status" is "ENABLED", it is judged that information processing cannot be continued in the information processing unit A (100)) at the main site, and processing can be switched to the processing in the information processing unit B (100) at the remote site. In this way, even in a case when the information processing service cannot be continued in prior art, the information processing service can be continuously provided.

The storage system 400 according to the present embodiment transmits/receives these heart beat signals 232 via the highly reliable second network 310, so reliability. can be improved.

Preferred embodiments of the present invention were described above, but the above mentioned embodiments were to make it easier to understand the present invention, and do not restrict the interpretation of the present invention. The present invention can be changed and improved within the scope of the essential character thereof, and the present invention includes equivalents thereof.

What is claimed is:

1. A storage system, comprising:
a first storage unit having a first storage volume for storing data; and
a second storage unit communicably coupled to the first storage unit and having a second storage volume for storing data, wherein
the first storage unit includes a data transmission unit configured to transmit replicated data to a storage unit when data is written to the first storage volume;
the second storage unit further includes a data reception unit configured to receive the replicated data and writing the replicated data to the second storage volume;
the first storage unit further includes a disk heart beat write unit configured to repeatedly write a first heart beat message to the first storage volume at intervals within a predetermined time; and
the second storage unit further includes a disk heart beat detection unit configured to detect a replication of the first heart beat message to be written to the second storage volume by the data reception unit;
wherein
a first information processing unit is communicably coupled to the first storage unit,
a second information processing unit is communicably coupled to the second storage unit,
the first information processing unit further comprises a node heart beat write request unit configured to repeatedly transmit a request to write a second heart beat message to the first storage volume, to the first storage unit at intervals within a predetermined time,
the first storage unit further comprises a node heart beat write unit configured to write the second heart beat message to the first storage volume according to the write request of the second heart beat message,
the second storage unit further includes a node heart beat transmission unit configured to transmit a replication of the second heart beat message to be written to the second storage volume by the data reception unit to the second information processing unit, and
the second information processing unit further comprises a node heart beat detection unit configured to detect the replication of the second heart beat message to be transmitted by the node heart beat transmission unit.

2. The storage system according to claim 1, wherein the first storage unit further comprises a disk heart beat creation unit configured to create disk heart beat signals to provide the first heart beat message.

3. The storage system according to claim 1, wherein the first information processing unit further comprises a node heart beat creation unit configured to create node heart beat signals to provide the second heart beat message.

4. The storage system according to claim 1, wherein:
the second storage unit further includes a disk heart beat detection result transmission unit configured to transmit a detection result of the replication of the first heart beat message by the disk heart beat detection unit to the second information processing unit, and
the second information processing unit further includes an operation status decision unit configured to determine operation status of a first computer system, the first computer system including the first information processing unit and the first storage unit, using detection of the first heart beat message and the second heart beat message.

5. The storage system according to claim 4, wherein the second information processing unit further comprises a fail-over control unit which transfers information processing from the first computer system to a second computer system, the second computer system including the second information processing unit and the second storage unit depending upon operation status of the first computer system.

6. The storage system according to claim 4, wherein
the second information processing unit further comprises an operation status display unit configured to provide the operation status of the first computer system to a user interface.

7. The storage system according to claim 1, wherein the first heart beat message includes at least one of: (1) identification information of the first heart beat message, (2) time information indicating when the first heart beat message was created, (3) first location information indicating a storage position of the first storage volume where the first heart beat message is written, and (4) second information indicating the storage position of the second storage volume where the first heart beat message is written.

8. A method for controlling a storage system which system includes a first storage unit having a first storage volume for storing data, and a second storage unit in communication with the first storage unit and having a second storage volume for storing data, wherein the first storage unit includes a data transmission unit configured to transmit replicated data to the second storage unit when the data is written to a first storage volume, and the second storage unit includes a data reception unit configured to receive the replicated data and writing the replicated data to the second storage volume, wherein a first information processing unit communicates with the first storage unit and a second information processing unit communicates with the second storage unit, the method comprising:
creating disk heart beat signals at the first storage unit to provide a first heart beat message;
creating node heart beat signals at the first information processing unit to provide a second heart beat message;
in the first storage unit, repeatedly writing the first heart beat message to the first storage volume at intervals;
in the second storage unit, detecting replicated first heart beat message to be written to the second storage volume;
repeatedly transmitting from the first information processing unit a request to write a second heart beat message to the first storage volume;
writing the second heart beat message to the first storage volume;
transmitting from the second storage unit to the second information processing unit a replication of the second heart beat message; and
at the second information processing unit, detecting the replication of the second heart beat message.

9. The method according to claim 8, further comprising:
from the second storage unit, transmitting a detection result of the first heart beat message to the second information processing unit; and
at the second information processing unit, determining operational status of a first computer system which includes the first information processing unit and the first storage unit using reception of the first heart beat message and the second heart beat message.

10. The method according to claim 9 further comprising transferring information processing from the first computer system to a second computer system which includes the second information processing unit and the second storage unit according to the operational status of the first computer system.

11. The method according to claim 9 further comprising at the second information processing unit providing the operational status of the first computer system to a user interface.

12. The method according to claim 8, wherein the first heart beat message comprises at least one of: (1) identification information of the first heart beat message; (2) time information indicating when the first heart beat message was created; (3) information indicating a storage position of the first storage volume; and (4) information indicating a storage position of the second storage volume.

13. A storage system comprising:
a first computer system including a first storage unit having a first storage volume for storing data, and a first information processing unit communicably coupled to the first storage unit; and
a second computer system including a second storage unit having a second storage volume for storing data, and a second information processing unit communicably coupled to the first storage unit; wherein
the first storage unit includes a data transmission unit configured to transmit replicated data to the second storage unit when the data is written to the first storage volume,
the second storage unit includes a data reception unit configured to receive the replicated data and writing the replicated data to the second storage volume,
the first storage unit includes a disk heart beat creation unit configured to repeatedly create a first heart beat message, and a disk heart beat write unit configured to repeatedly write the first heart beat message to the first storage volume at intervals;
the second storage unit further includes a disk heart beat detection unit configured to detect the replicated first heart beat message, and a disk heart beat detection result transmission unit configured to transmit a signal indicating receipt of the replicated first heart beat message by the disk heart beat detection unit to the second information processing unit;
the first information processing unit includes a node heart beat creation unit configured to repeatedly create a second heart beat message, and a node heart beat write request unit configured to repeatedly transmit a request to write the second heart beat message to the first storage volume;
the first storage unit includes a node heart beat write unit configured to write the second heart beat message to the first storage volume according to the write request of the second heart beat message;
the second storage unit includes a node heart beat transmission unit configured to transmit to the second information processing unit the replication of the second heart beat message written to the second storage volume by the data reception unit;
the second information processing unit includes a node heart beat detection unit configured to detect the replication of the second heart beat message, and an operation status unit configured to determine operational status of the first computer system according to the second heart beat message and the first heart beat message, and a fail-over execution unit configured to transfer information processing from the first computer system to the second computer system according to the operational status of the first computer system.

14. The storage system according to claim 13, wherein:
the first heart beat message includes at least one of: (1) identification information of the first heart beat message, (2) time information indicating when the first heart beat message was created, (3) information indicating a storage position of the first storage volume, and (4) information indicating a storage position of the second storage volume; and the second heart beat message includes at least one of: (1) identification information of the second heart beat message, (2) time information indicating when the second heart beat message was created, (3) information indicating a storage position of the first storage volume, and (4) information indicating a storage position of the second storage volume.

* * * * *